(12) United States Patent
Ruffner et al.

(10) Patent No.: US 6,586,180 B1
(45) Date of Patent: Jul. 1, 2003

(54) DIRECTED ANTISENSE LIBRARIES

(75) Inventors: Duane E. Ruffner, Salt Lake City, UT (US); Michael L. Pierce, Salt Lake City, UT (US); Zhidong Chen, Salt Lake City, UT (US)

(73) Assignee: University of Utah, Salt Lake City, UT (US)

( * ) Notice: Subject to any disclaimer, the term of this patent is extended or adjusted under 35 U.S.C. 154(b) by 186 days.

(21) Appl. No.: 09/647,344

(22) PCT Filed: Mar. 28, 1999

(86) PCT No.: PCT/US99/06742

§ 371 (c)(1),
(2), (4) Date: Dec. 4, 2000

(87) PCT Pub. No.: WO99/50457

PCT Pub. Date: Oct. 7, 1999

Related U.S. Application Data

(60) Provisional application No. 60/107,504, filed on Nov. 6, 1998, and provisional application No. 60/079,792, filed on Mar. 28, 1998.

(51) Int. Cl.[7] .............................. C12Q 1/68; C07H 21/00
(52) U.S. Cl. .......................... 435/6; 435/6; 435/91.31; 435/320.1; 435/375; 536/23.1; 536/23.2; 536/24.3; 536/24.33; 536/24.5
(58) Field of Search ..................... 435/6, 91.31, 320.1, 435/375; 536/23.1, 23.2, 24.3, 24.33, 24.5

(56) References Cited

U.S. PATENT DOCUMENTS 5,496,698 A * 3/1996 Draper et al. .................. 435/6

OTHER PUBLICATIONS

Hasan et al., Gene (1986) 50: 55–62.*

* cited by examiner

*Primary Examiner*—Andrew Wang
*Assistant Examiner*—James Douglas Schultz
(74) *Attorney, Agent, or Firm*—Clayton, Howarth & Cannon, P.C.

(57) ABSTRACT

A method for making a directed antisense library against a target transcript is described. A cDNA of the target transcript is cloned in an appropriate cloning vector. Next, a plurality of deletion derivatives of the cloned cDNA is prepared such that the deletions serially extend into the cDNA from one end thereof. The resulting deletion library is then treated such that cDNA is removed from the other end of each cDNA insert, thus obtaining a fragment library having fragments of a selected size. A catalytic core is then inserted into each fragment of the fragment library, resulting in the directed antisense library. An illustrative antisense gene in the hammerhead ribozyme catalytic core. Plasmids for making the antisense library, plasmids and methods for making the fragment library, and a method for identifying target sites for antisense-mediated gene inhibition are also described.

8 Claims, 8 Drawing Sheets

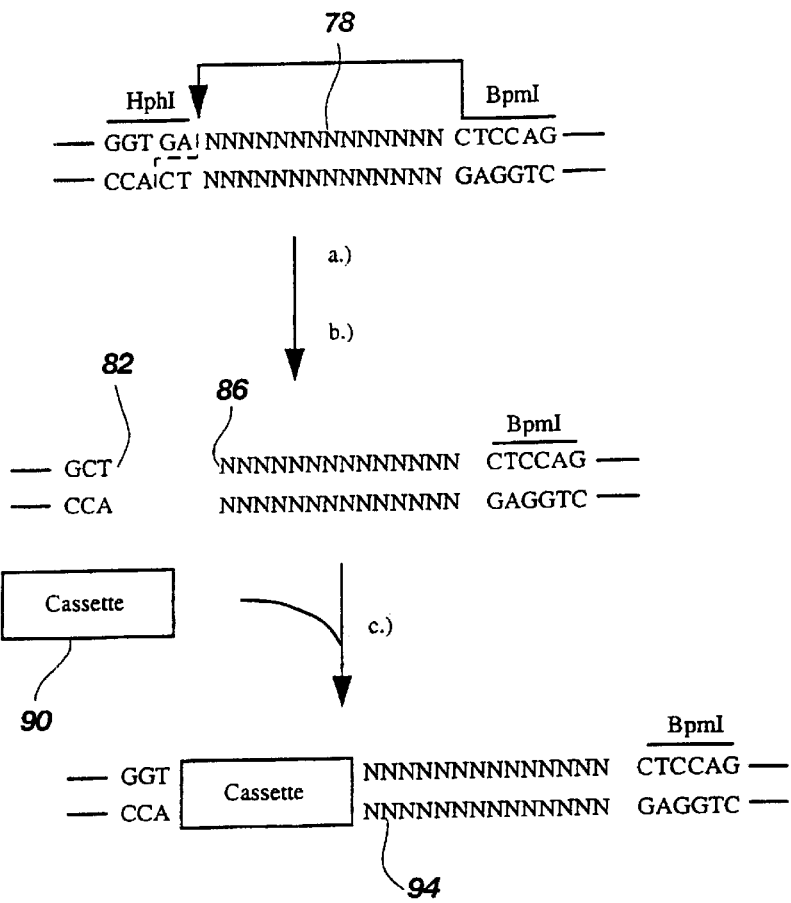
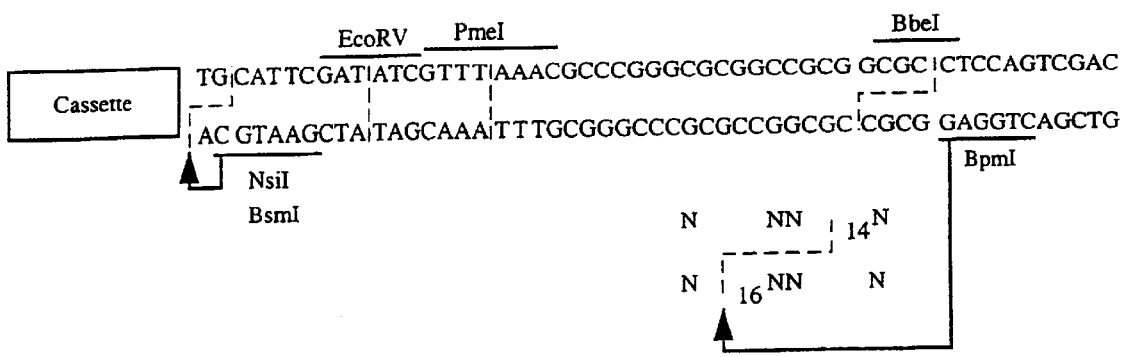
Fig. 5A
Fig. 5B

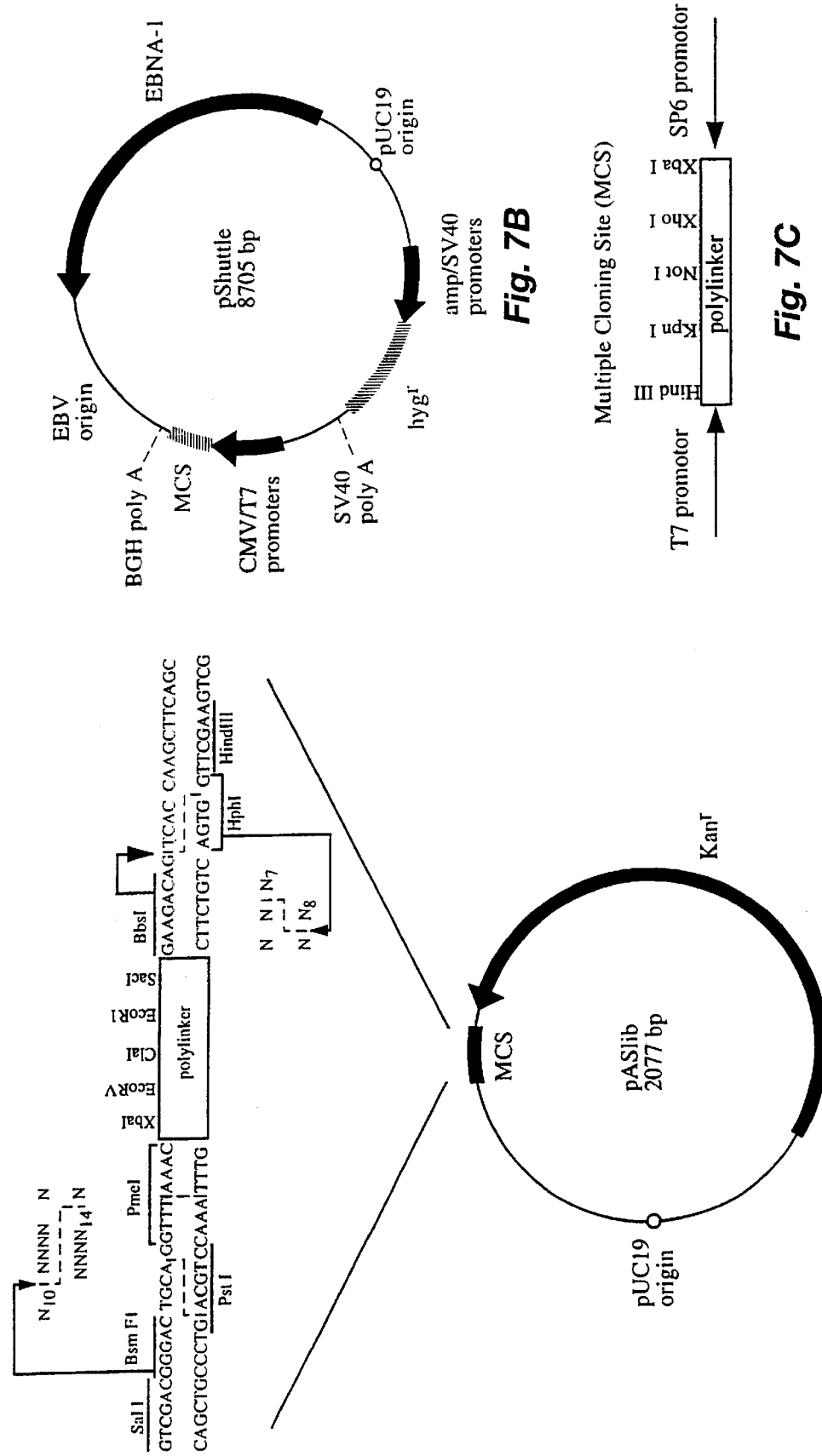

DIRECTED ANTISENSE LIBRARIES

CROSS-REFERENCE TO RELATED APPLICATIONS

This application is an application under 35 U.S.C. §371 of International Application No. PCT/US99/06742, which has an international filing date of Mar. 28, 1999, which claims the benefit of U.S. Provisional Application No. 60/079,792, filed Mar. 28, 1998, and U.S. Provisional Application No. 60/107,504, filed Nov. 6, 1998.

STATEMENT REGARDING FEDERALLY SPONSORED RESEARCH OR DEVELOPMENT

This invention was made with government support under Grant No. 1R03RR08849 awarded by the National Institutes of Health. The government has certain rights in the invention.

BACKGROUND OF THE INVENTION

This invention relates to antisense agents. More particularly, the invention relates to compositions and methods for generation of directed antisense libraries and methods of use thereof wherein the antisense agents in the libraries can potentially bind to every binding site on a selected RNA transcript.

Antisense RNA, DNA, and ribozymes have been widely studied as research tools and potential therapeutic agents for inhibiting the expression of specific genes. These agents operate by binding to a complementary region on an RNA transcript produced from the gene of interest. On binding, the antisense agent can prevent expression of the RNA, and this can occur through a variety of different mechanisms. There are many sites on any given RNA for targeted inhibition by an antisense molecule. For a typical RNA transcript of 2000 nucleotides, just under 2000 target sites are available. Examination of a few to tens of randomly chosen target sites reveals a great variability in activity. Clearly, not all target sites are equivalent in their ability to permit antisense mediated inhibition. Consequently, identification of effective target sites on the RNA transcript for interaction with the antisense molecule is imperative for successful application of antisense technology. Methods currently available for this purpose include the use of computer algorithms to predict target accessibility based on the predicted secondary structure of the mRNA, the use of randomized oligonucleotide and ribozyme libraries in cell free systems, and the examination of a few to tens of antisense oligonucleotides, targeted to arbitrarily chosen sites, in cell culture assays. These approaches have met with limited success.

To identify the most effective target site(s), the following conditions should be met. First, all possible sites on the target RNA should be evaluated Second, evaluation should be carried out in the normal cellular milieu. This insures that the target is in its natural structure, associated with its normal complement of cellular factors. Additionally, the antisense agent has the opportunity to act on alternate structures that may arise as a result of the many RNA processing reactions.

To evaluate all target sites, antisense libraries must be used. These libraries should contain antisense molecules targeted to every site. One approach is the use of completely randomized DNA, RNA, or ribozyme libraries. The use of completely randomized libraries suffers from two major disadvantages. First, while such libraries may contain antisense molecules directed at all sites on the target RNA, they also contain antisense molecules directed at all sites of all potential RNA transcripts produced by the cell. Therefore, these random libraries potentially have the capability to inhibit expression of every gene in the cell. Because of this, random libraries are limited to in vitro use in cell free assays. Second, the complexity of these libraries is enormous. For example, a random library that uses 14 nucleotides to recognize its target must contain at least $2.6 \times 10^8$ (i.e., $4^{14}$) different members. Realistically, the size of the library must be at least 10- to 100-fold greater in size to insure representation of all sequences. The production and screening of such large libraries is likely beyond current capabilities.

Herein there is described a new method for identifying optimal antisense target sites against any desired RNA transcript This is a directed library approach. In other words, this approach uses an antisense library that targets every site on any selected RNA and only sites present on the selected RNA. This library, therefore, does not inhibit other non-target RNA transcripts. This approach is also an improvement over known methods because it uses relatively small libraries. For example, a library targeting an RNA transcript of 2000 nucleotides, and using 14 nucleotides to recognize its target, theoretically needs 1986 members. In practice, the library would need to be 10- to 50-times this size. At 50 times, or 99,300 members, this is still a relatively small library. These directed libraries can be used in both in vitro and in vivo assays for the detection of effective target sites for antisense mediated gene inhibition.

In view of the foregoing, it will be appreciated that a method for generating directed antisense libraries would be a significant advancement in the art. Herein is described a method for examining the entire length of any RNA transcript for sites that are accessible to antisense agents. This approach allows for the localization of the most effective sites for targeting with antisense agents.

BRIEF SUMMARY OF THE INVENTION

It is an object of the present invention to provide a simple and inexpensive method for producing directed antisense libraries against any selected RNA transcript.

It is also an object of the invention to provide a method of producing directed antisense libraries wherein such libraries contain antisense agents directed against all targets spanning the entire selected RNA transcript.

It is another object of the invention to provide a method of using directed antisense libraries for locating efficient target sites on the selected RNA transcript.

It is still another object of the invention to provide compositions for use in constructing directed antisense libraries.

It is yet another object to provide a method for making fragment libraries of a selected size of DNA fragment inserted in a cloning vector.

These and other objects can be addressed by providing a method for generating an antisense library targeted to a selected RNA transcript comprising:

(a) preparing a double-stranded cDNA, comprising a first end, a second end, and a central site thereof, from the selected RNA transcript and cloning the cDNA in a cloning vector comprising a promoter configured such that an antisense transcript of the cDNA is synthesized upon transcription mediated by the promoter, resulting in a cloned cDNA;

(b) creating a plurality of deletion derivatives of the cloned cDNA wherein each of the plurality of deletion derivatives has a deletion extending from the first end into the cloned cDNA such that the plurality of deletion derivatives comprises a deletion library comprising deletions extend serially into the cDNA;

(c) reducing the size of the cDNA contained in the deletion library to a preselected size by removing a portion of the cDNA from the second end thereof to result in a fragment library;

(d) inserting an antisense gene DNA into the central site of the cDNA in the fragment library, thereby obtaining the antisense library.

Preferred cloning vectors comprise multi-cloning sequences comprising SEQ ID NO:1 and a combination of SEQ ID NO:2 and SEQ ID NO:3. In a preferred embodiment of the invention, the deletion derivatives are created with exonuclease III resection of the cloned cDNA. The size of the cDNA contained in the deletion library is preferably reduced to a preselected size by digesting the deletion library with a type IIS restriction endonuclease. Further, inserting the antisense gene DNA into the central site of the cDNA in the fragment library preferably comprises digesting the fragment library with a type IIS restriction endonuclease, thereby creating the central site, and ligating the antisense gene DNA at the central site. A preferred antisense gene comprises a ribozyme catalytic core, more preferably, a hammerhead ribozyme catalytic core.

Another aspect of the invention relates to a method for generating a library of DNA fragments of a selected size wherein the fragments collectively span all possible sites of the selected size in a source DNA comprising a first end, a second end, and a central site thereof, comprising:

(a) cloning the source DNA in a cloning vector, (b) creating a plurality of deletion derivatives of the cloned source DNA wherein each of the plurality of deletion derivatives has a deletion extending from the first end into the cloned DNA such that the plurality of deletion derivatives comprises a deletion library comprising deletions extend serially into the cloned DNA; and (c) reducing the size of the DNA contained in the deletion library to a preselected size by removing a portion of the DNA from the second end thereof to result in the library of fragments.

Still another aspect of the invention relates to a method for identifying target sites for antisense-mediated inhibition of a selected gene comprising:

(a) constructing a directed antisense library targeted at the selected gene wherein the library is contained in a cloning vector having a promoter configured for transcribing antisense transcripts from the directed antisense library in suitable cells wherein the selected gene is expressed as a target transcript;

(b) transforming a plurality of the suitable cells such that each of the plurality of suitable cells transcribes an antisense transcript that has access to the target transcript for potential inactivation thereof;

(c) identifying a cell wherein an antisense transcript inactivates the target transcript; and (d) analyzing the antisense transcript that inactivates the target transcript and determining a target site on the antisense transcript that is associated with inactivation of the target transcript.

Yet another aspect of the invention relates to a method for identifying target sites for antisense-mediated inhibition of a selected gene comprising:

(a) constructing a directed antisense library targeted at the selected gene wherein the library is contained in a cloning vector having a promoter configured for transcribing antisense transcripts from the directed antisense library in vitro;

(b) transcribing antisense transcripts from the directed antisense library in vitro;

(c) incubating the antisense transcripts with a lysate from a cell containing target transcripts transcribed from the selected gene such that antisense transcripts targeted to the target transcripts bind to such target transcripts; and (d) analyzing the antisense transcripts that bind the target transcript and determining a target site on the antisense transcript that is associated with binding of the target transcript.

BRIEF DESCRIPTION OF THE SEVERAL VIEWS OF THE DRAWINGS

FIG. 5A shows an illustrative method for inserting a selected cassette at an end of a deletion fragment (SEQ ID NO:49) in a deletion fragment library (SEQ ID NO:39) according to the present invention.

FIG. 5B shows an illustrative method for inserting a selected cassette in a MCS (SEQ ID NO:50) prior to preparation of a deletion fragment library according to the present invention.

FIG. 7A shows a map of vector pASlib according to the present invention, including sequences of relevant MCS regions (SEQ ID NO:2, SEQ ID NO:3).

FIG. 7B shows a map of vector pShuttle according to the present invention.

FIG. 7C shows a map of the MCS of pShuttle according to the present invention.

DETAILED DESCRIPTION

Before the present compositions and methods for generating directed antisense libraries and methods of use thereof are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise.

In describing and claiming the present invention, the following terminology will be used in accordance with the definitions set out herein.

As used herein, "antisense agent" and similar terms mean antisense RNA, antisense DNA, and ribozymes.

As used herein, "comprising," "including," "containing," "characterized by," and grammatical equivalents thereof are inclusive or open-ended terms that do not exclude additional, unrecited elements or method steps. "Comprising" is to be interpreted as including the more restrictive terms "consisting of" and "consisting essentially of."

As used herein, "consisting of" and grammatical equivalents thereof exclude any element, step, or ingredient not specified in the claim.

As used herein, "consisting essentially of" and grammatical equivalents thereof limit the scope of a claim to the specified materials or steps and those that do not materially affect the basic and novel characteristic or characteristics of the claimed invention.

Construction of Directed Antisense Libraries

Figure 1A:
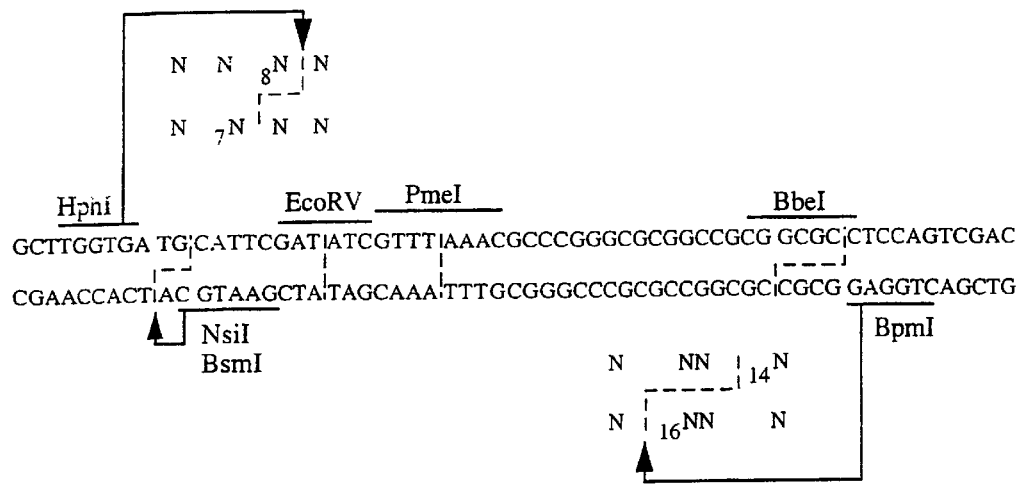
FIGS. 1A and 1B show illustrative multi-cloning sequences (MCS's; SEQ ID NO:1, SEQ ID NO:2, SEQ ID NO:3) according to an aspect of the present invention.

The present invention includes a procedure that allows construction of directed antisense libraries of a variety of types. This requires the use of specially designed bacterial and/or mammalian plasmid vectors. Most importantly, these vectors possess a specially designed multi-cloning sequence (MCS). This approach is not restricted to a single MCS, as many can be designed that allow the procedure to be performed. Two illustrative MCS's are shown in FIGS. 1A (SEQ ID NO:1) and 1B (SEQ ID NO:2 and SEQ ID NO:3). These simply illustrate two possible multi-cloning sequences that could be used for this method. While some of the same restriction enzyme sites are used in both of these MCS's, such particular sites are not necessarily the only sites that could be used. Many other restriction enzyme sites could substitute for any of the restriction sites, allowing the same procedure to be performed.

The procedure uses a special multi-cloning sequence and a series of enzymatic manipulations to produce DNA fragment libraries directed against any desired gene of interest. The fragment libraries contain all overlapping fragments spanning the entire length of the gene of interest Transcription in vitro or in vivo of the DNA fragment allows the production of an antisense RNA targeted to the site on the RNA transcript that is encoded by the DNA fragment. Transcription of the entire DNA fragment library produces all antisense RNA molecules targeting all positions on the RNA target. Expression of the library in mammalian cells allows identification of effective target sites for antisense-mediated gene inhibition.

Figure 2:
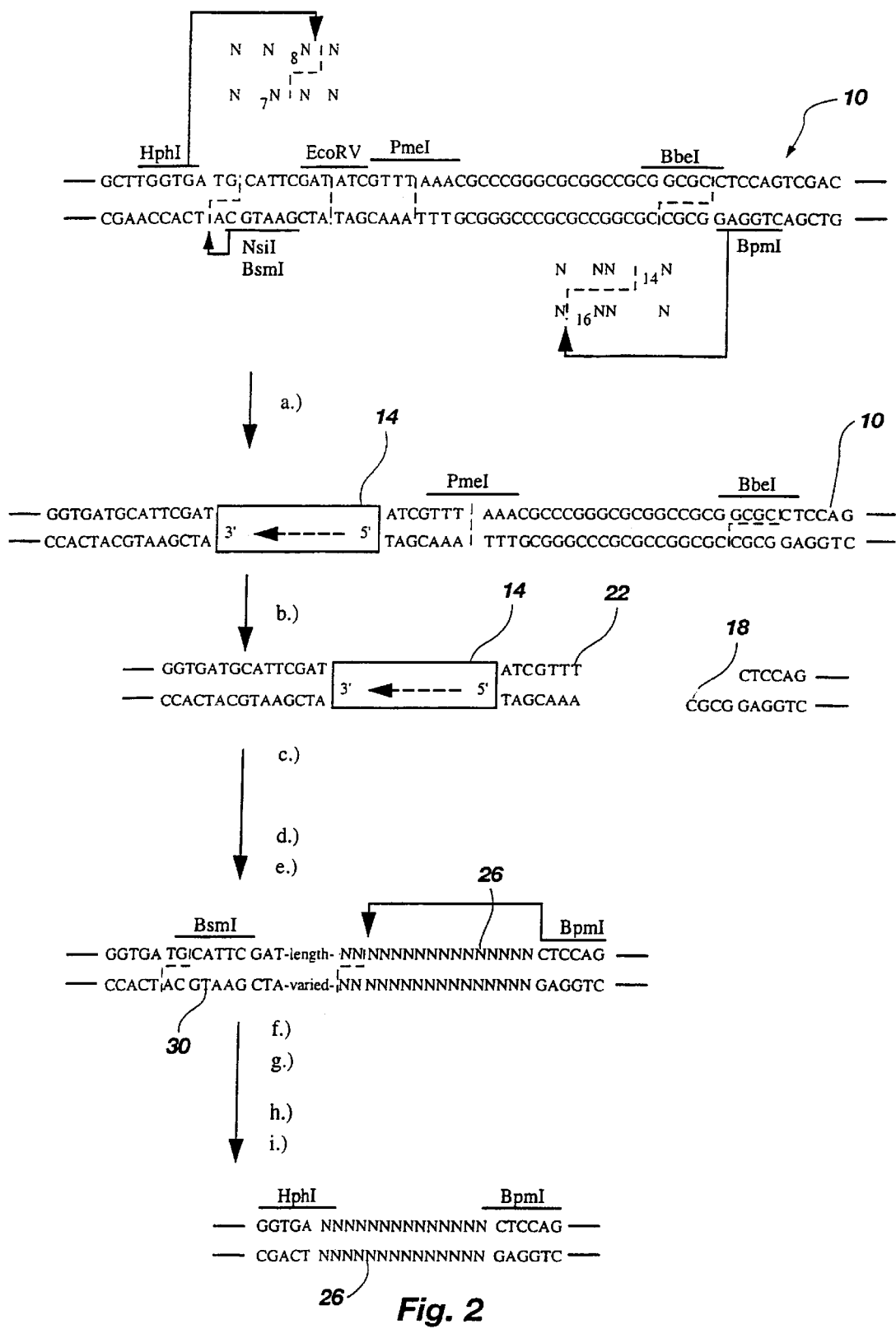
FIG. 2 summarizes an illustrative method for making a DNA fragment library (SEQ ID NO:39) containing 14 bp fragments using the MCS of FIG. 1A (SEQ ID NO:1) according to the present invention; also shown are intermediates in the construction of the DNA fragment library (SEQ ID NO:35 through SEQ ID NO:38).

The procedure is illustrated in FIG. 2 using the MCS shown in FIG. 1A. Beginning with the MCS 10 in a suitable circular plasmid vector (described in more detail below), a blunt-ended DNA fragment encoding the gene of interest 14 is ligated into the EcoRV-digested MCS (FIG. 2, step a). Since the gene can be inserted in one of two orientations, a clone is selected, according to methods well known in the in art such as nucleotide sequencing or restriction mapping, wherein the gene insert is suitably oriented. The orientation will depend on the placement of a transcriptional promoter adjacent to the MCS. The orientation of the insert will be chosen such that the antisense strand of the insert will be transcribed by the adjacent promoter. Next, a deletion library is prepared. The plasmid containing the gene of interest is digested with both PmeI and BbeI (FIG. 2, step b). The BbeI terminus is protected from exonuclease III digestion because of its 3' overhang 18, while the PmeI terminus 22 is a suitable substrate therefor. The digested plasmid is then treated with exonuclease III and aliquots are removed over time into a stop mixture (FIG. 2, step c). The time points are chosen such that deletions are generated after every nucleotide across the entire gene. After exonuclease III digestion, the combined aliquots are treated with mung bean nuclease to remove the resulting 5' overhang (FIG. 2, step c). The termini are then polished with T4 DNA polymerase (FIG. 2, step d) and the plasmid is re-circularized with T4 DNA ligase to produce the deletion library (FIG. 2, step e). The deletion library is then converted into a fragment library (14 base-pair fragments 26 in this case) by digestion with restriction endonucleases BsmI and BpmI (FIG. 2, step f), purification of the plasmid containing the 14 bp fragment 26 from the excised BpmI/BsmI fragment 30 (FIG. 2, step g), end-polishing with T4 DNA polymerase (FIG. 2, step h), and ligation with T4 DNA ligase (FIG. 2, step i). Not stated, but implied, after each ligation step (i.e., steps a, e, and i) the ligation mixture is transformed into bacteria, the DNA is recovered from the bacteria, and the recovered DNA is used in the subsequent step. All of these reactions involving restriction endonucleases, ligases, polymerases, nucleases, and the like are well known in the art and are performed according to standard methods, e.g., J. Sambrook et al., Molecular Cloning: A Laboratory Manual (2d ed., 1989); T. Maniatis et al., Molecular Cloning: A Laboratory Manual (1982); F. Ausubel et al., Current Protocols in Molecular Biology (1987), relevant parts of which are hereby incorporated by reference.

The essence of the procedure is as follows. A gene of interest is converted into a library of fragments serially deleted after every nucleotide. This deletion library is subsequently converted into a fragment library containing all overlapping fragments encoded by the gene.

The fragment library can also serve as the starting point for construction of other types of antisense libraries. One such library is an antisense hammerhead ribozyme library.

Figure 3:
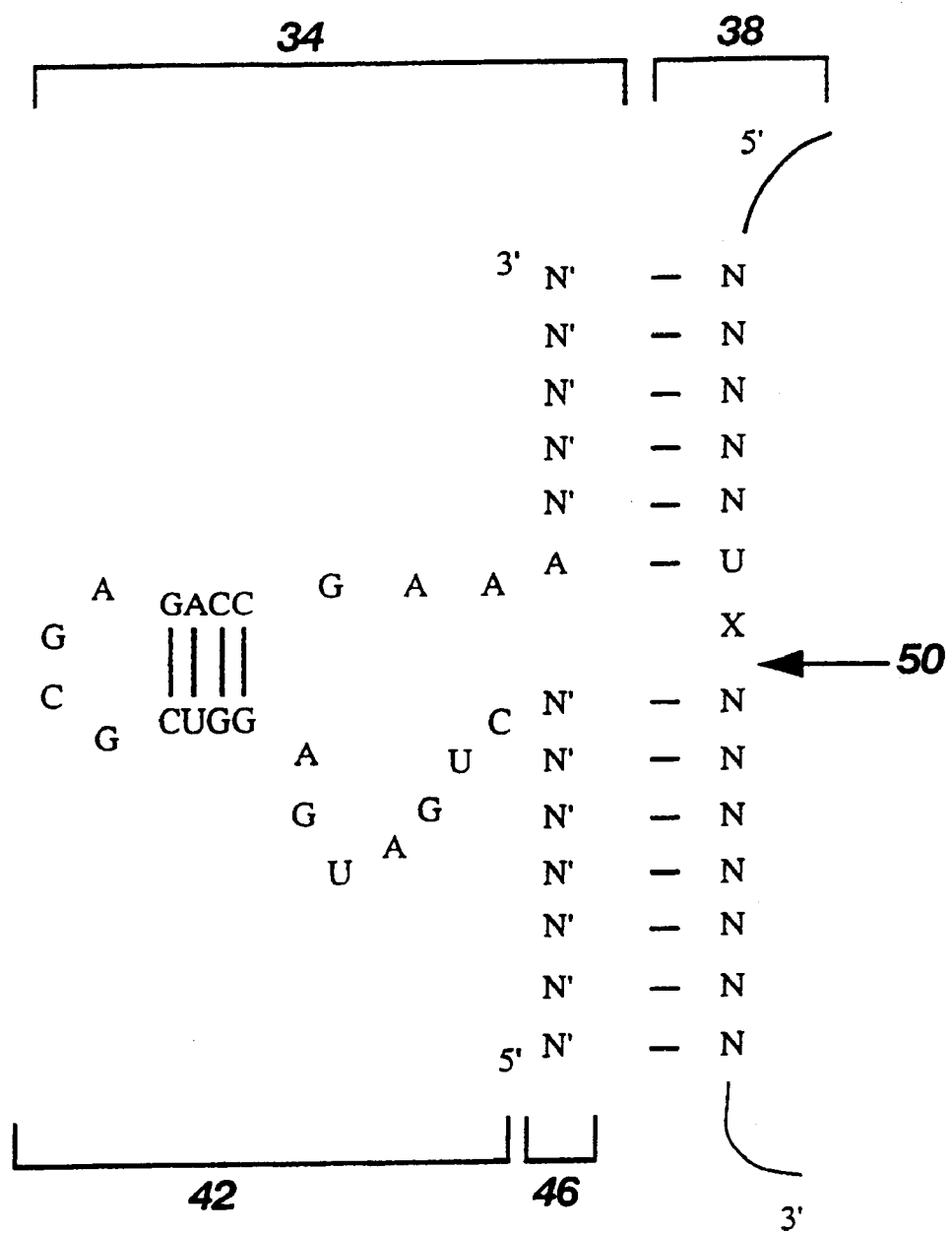
FIG. 3 shows a schematic representation of a hammerhead ribozyme (SEQ ID NO:40) bound to a target substrate (SEQ ID NO:41), wherein X represents A, C, or U; the hammerhead ribozyme comprises a catalytic core that cleaves the substrate at the cleavage site indicated by the arrow and a recognition domain for binding to the substrate by base pairing.

A hammerhead ribozyme 34 is a small RNA that can catalyze the cleavage of a complementary RNA target 38 (FIG. 3). The hammerhead comprises a catalytic core 42 (SEQ ID NO:4), essential for cleavage activity. Additionally, the hammerhead has a recognition domain 46 that is required for interaction with a complementary substrate, such as an RNA transcript. There are few sequence requirements for the recognition domain, thus by changing the sequence of the recognition domain almost any sequence can be targeted for cleavage by the hammerhead. Cleavage of the substrate 38 occurs at a cleavage site 50 containing an NUH sequence (where N is A, C, G, or U and H is A, C, or U). In the case where the substrate is a gene transcript, the hammerhead can be used as an antisense inhibitor of gene expression.

Figure 4:
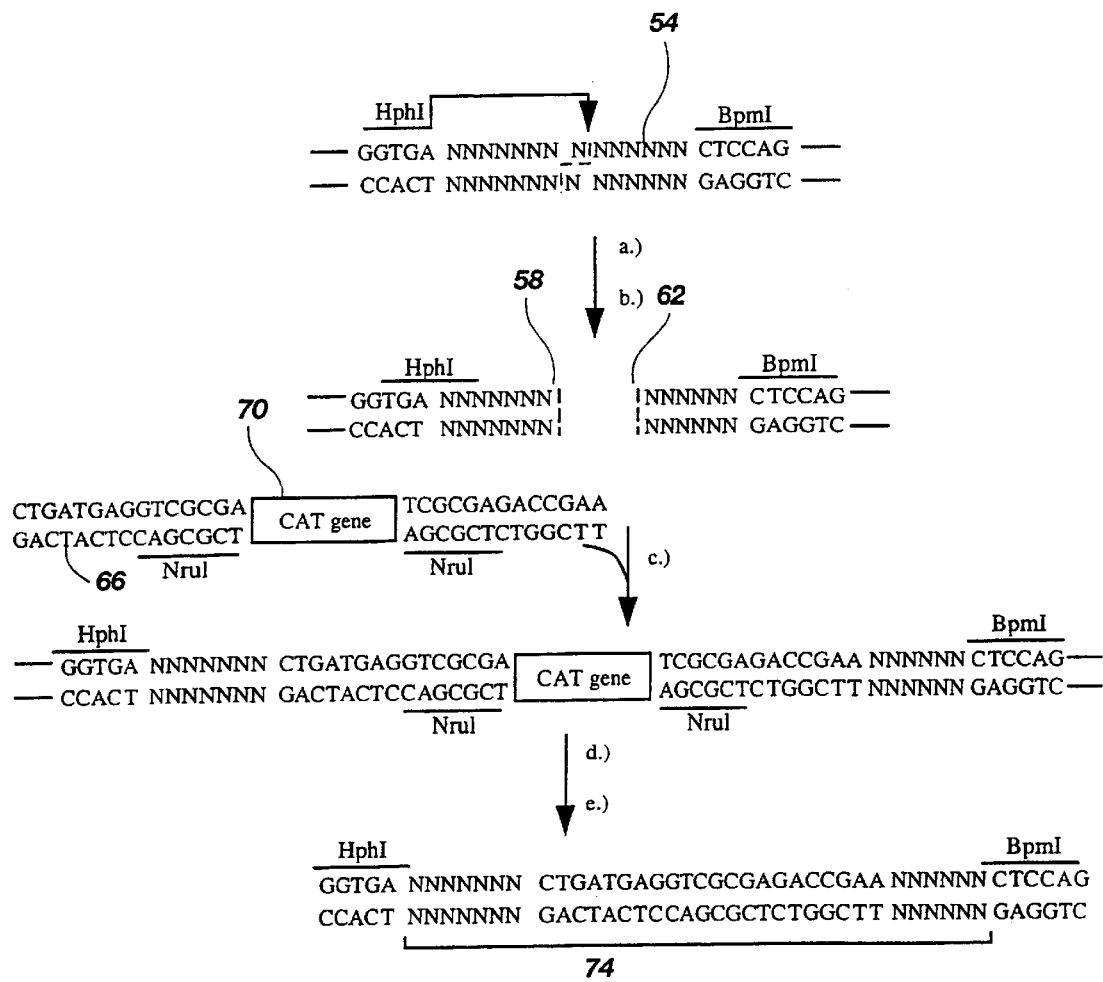
FIG. 4 summarizes an illustrative method for making a hammerhead ribozyme library (SEQ ID NO:48) from an antisense RNA library (SEQ ID NO:39) according to the present invention; also shown are intermediates in the construction of the hammerhead ribozyme library (SEQ ID NO:42 through SEQ ID NO:47).

To convert the fragment (antisense RNA) library into a hammerhead ribozyme library, a DNA fragment encoding the hammerhead catalytic core is inserted into the DNA fragment encoding the antisense RNA. This is performed as illustrated in FIG. 4. The 14 base-pair fragment 54 in the fragment library is bisected with HphI (FIG. 4, step a). The resulting single-stranded overhang on each terminus is then removed using the 3' to 5' exonuclease activity of T4 DNA polymerase (FIG. 4, step b) to result in blunt ends 58, 62. A DNA fragment encoding the hammerhead catalytic core 66 (SEQ ID NO:4) is then inserted by ligation (FIG. 4, step c). The catalytic core shown in FIG. 4 is interrupted by a promoter-less chloramphenicol resistance gene 70 (CAT). A promoter is provided flanking the MCS. Transforming bacteria and selecting for chloramphenicol resistance allows selection for clones in which the catalytic core is in the correct orientation to produce a bonafide hammerhead ribozyme. Next, the CAT gene is removed and the sequence encoding a hammerhead ribozyme 74 is generated by NruI digestion (FIG. 4, step d) and ligation with T4 DNA ligase (FIG. 4, step e).

Other types of antisense libraries can also be produced from the fragment library. For instance, other cassettes can be ligated into an HphI-digested fragment library. Catalytic cores from other ribozymes, including those currently known and those to be discovered, can be inserted. Additionally, other cassettes could be used that encode sequences that cause modification to the target by mechanisms other than cleavage. Similarly, ribozyme and non-ribozyme sequences can be added to the end of the antisense sequence. This is illustrated in FIG. 5A, wherein the DNA fragment library is digested with BpmI, which digests the DNA at the distal end of the inserted fragment 78 (step a). The unpaired nucleotides resulting from this reaction are then removed with T4 DNA polymerase (step b) to result in blunt ends 82, 86. Next, a cassette 90 is inserted by ligation to recircularize the modified plasmid 94, now containing the cassette inserted at an end of the insert fragment. Alternatively, instead of inserting a cassette after the fragment library is produced, a suitable cassette can be engineered into the starting multi-cloning sequence. For instance, the HphI site of the original MCS (FIG. 1A) could be replaced with a cassette encoding any desired sequence (FIG. 5B). Then, using the same procedure illustrated in FIG. 2, the cassette can be placed against the fragment sequence in the conversion of the deletion library into the fragment library. An example of a possible cassette is one encoding the sequence CUGA. An antisense RNA with this sequence at its 3' end has been shown to be capable of directing the 2'-O-methylation of the complementary target (J. Cavaille et al., Targeted ribose methylation of RNA in vivo directed by tailored antisense RNA guides, 383 Nature 732–735 (1996)). This reaction is catalyzed by modification machinery present in mammalian cells. 2'-O-methylation of a suitable target site could be used to inhibit expression of the RNA transcript. Other cellular RNA processing reactions can also be used in a similar fashion with the use of different cassettes placed adjacent to the antisense RNA sequence.

Use of Directed Libraries in the Identification of Target Sites for Antisense-Mediated Gene Inhibition Antisense libraries prepared according to the present invention can be assayed in vitro in a cell free system or in vivo in cultured cells, as will be described in more detail below.

In vivo assay. For in vivo, use the antisense library is introduced by transfection into a suitable cell line that expresses the gene of interest. The transfection conditions are chosen such that only one member of the library is taken up by each individual cell. The individual cells then each express a different antisense molecule targeted to a different site on the RNA transcript of interest. All target sites are represented in the entire cell population produced by transfection. Using a suitable detection method, cell clones can be identified in which expression of the target RNA has been reduced or eliminated. These clones possess an antisense molecule that targets an effective site on the RNA transcript of interest. The plasmid encoding this antisense molecule is recovered and the target sequence is identified by DNA sequencing.

Figure 6A:
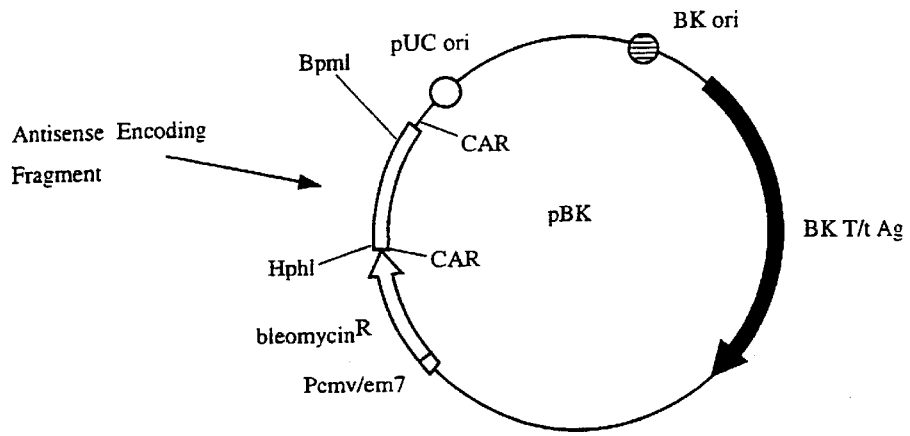
FIG. 6A shows a map of expression vector pBK, which is suitable for use in identifying antisense targets in mammalian cells according to the present invention.

To identify suitable targets in vivo, specially designed expression vectors are required. One key feature of such expression vectors is that they are designed to replicate episomally in mammalian cells. FIGS. 6A and 7B show two such episomal vectors, pBK (SEQ ID NO:17) and pShuttle (SEQ ID NO:14), respectively. Vector pBK possesses the origin of replication and the gene encoding the T/t antigen from the human papova virus BK (BKV). Vector pShuttle possesses the origin of replication and the EBNA1 gene from the human Epstein-Barr virus (EBV). These sequence elements allow each of the plasmids to replicate extrachromosomally (episomally). Episomal expression is desirable for several reasons. First, it eliminates the clone-to-clone variation in expression that occurs if stable transfectants are used P. B. Belt et al., 84 Gene 407–417 (1989). Second, since the copy number of the episomal vector is determined primarily by the transfection conditions and, once established, remains tightly regulated, J. L. Yates & N. Guan, 65 J. Virol. 483–488 (1991), then effects on expression due to differences in copy number are minimal. Consequently, the selection of antisense efficacy is based on accessibility and not the level of expression. Third, the use of an episomal expression vector allows for high transfection efficiency. P. B. Belt et al., 84 Gene 407–417 (1989); R. F. Maragolskee et al., 8 Mol. Cell. Biol. 2837–2847 (1988). This is important to ensure that all antisense agents present in the library are represented in the mammalian transfectants. Finally, the plasmid can be recovered and shuttled back into bacterial cells. This allows the sequence of effective antisense agents to be determined, thereby identifying accessible target sites. As a demonstration of episomal replication, pShuttle was used to transfect HeLa cells, and the cells were grown in culture under 400 µg/ml hygromycin selection. After 1 month in culture, low molecular weight DNA was isolated from $1\times10^7$ cells and used to transform *Escherichia coli* DH5α, producing a total of 2475 hygromycin-resistant colonies.

Figure 6B:
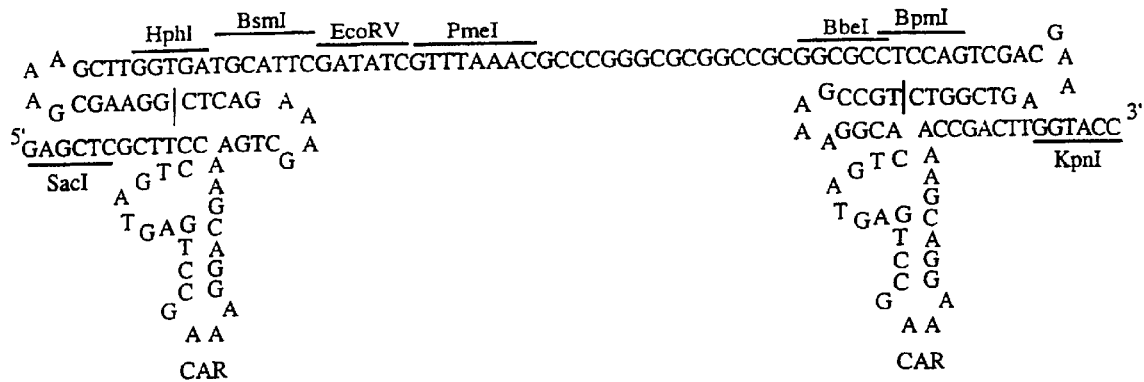
FIG. 6B shows base pairing of nucleotides in a multi-cloning sequence flanked by cis-acting ribozymes (CAR's) (SEQ ID NO:18).

Vector pBK illustrates other features of value for in vivo expression of antisense libraries. pBK has a single antibiotic resistance gene, bleomycin$^R$, driven by dual mammalian (CMV) and bacterial (em7) promoters. This allows the same selectable marker to be used in both bacterial and mammalian cells. This helps to minimize the size of the vector, since large vectors transfect at a lower efficiency. pBK has both the BK origin of replication and the origin of replication from the pUC series of bacterial plasmids. Therefore pBK can be replicated in both bacterial and mammalian cells, and can be shuttled between them. pBK was designed such that the antisense library could be constructed and expressed from the same vector. The antisense sequence is expressed by read-through expression of the bleomycin$^R$ gene. This ensures expression of the antisense agent when the cells are grown in the presence of bleomycin. The antisense fragment is released from the larger bleomycin transcript by the activity of cis-acting ribozymes (CAR), hammerhead ribozymes in this case, that flank the antisense sequence. In the absence of CAR, flanking sequences of the larger bleomycin transcript could inhibit the activity of the antisense agent. Sequences outside of the MCS (FIG. 1A) encode the cis-acting ribozymes. They are illustrated in FIG. 6B where only the sequence of the upper strand of the MCS is shown (SEQ ID NO:18). On cleavage by the CAR, the antisense agent is released and stable hairpin loops form to increase the nuclease resistance of the antisense agent.

pShuttle shares many of the same features as pBK, with two significant differences. First, this episomal vector is EBV-based rather than BKV-based. The second and more significant difference is that construction of the antisense library is not possible in pShuttle. Instead, the antisense library is first constructed in pASlib (SEQ ID NO:7), and subsequently transferred to pShuttle for expression in mammalian cells. The antisense encoding fragment of pASlib is removed by digestion with HindIII and SalI (FIG. 7A). Subsequently, the HindIII/SalI fragment is ligated into the multi-cloning site of pShuttle via the HindIII and XhoI sites (FIG. 7C). This places the antisense sequence downstream of a dual CMV/T7 promoter for expression in vivo in mammalian cells or, alternatively, in vitro by transcription using T7 RNA polymerase.

Although it is believed that episomal shuttle vectors are advantageous for expression of directed antisense libraries, viral vectors can also be used. Many viruses are currently being examined for expression of foreign genes for the purpose of gene therapy. These same viral vectors would be suitable for expression of directed antisense libraries. Some of these vectors replicate extrachromosomally and therefore behave similarly to the described episomal vectors. Others integrate into chromosomes. For the use of integrative viral vectors, two minor problems would need to be dealt with. First, the antisense gene present within the viral vector would integrate into the chromosome with the virus. Consequently, recovering the gene to determine the site at which it targets is not readily possible. This can be dealt with by using polymerase chain reaction (PCR) to amplify the integrated antisense gene. The PCR product could be sequenced directly, or cloned and sequenced to identify the target site. Second, some of these viral vectors integrate randomly and this would produce differing levels of expression from different members of the directed antisense library. As discussed, it is important that expression of all members of the library be comparable. This problem can be dealt with by using a viral vector that integrates at a specific preferred site, such as adeno-associated virus.

In vitro assay. Identification of effective antisense target sites using antisense libraries can also be performed using in vitro assays. For instance, an assay such as that used by Lieber and Strauss (A. Lieber & M. Strauss, Selection of efficient cleavage sites in target RNAs by using a ribozyme expression library, 15 Molecular and Cellular Biology 540–551 (1995)), can be used. For this, the antisense library is produced by in vitro transcription from a suitable promoter. In the present case, an antisense ribozyme library in pShuttle might be used. Of course other types of antisense libraries could be used similarly. The library-containing pShuttle is digested with XbaI and used as a template for run-off transcription of the antisense ribozyme by in vitro transcription with T7 RNA polymerase, according to methods well known in the art (e.g., C. J. Noren et al., 18 Nucleic Acids Res. 83–88 (1990). Subsequently, the transcribed ribozyme library is incubated in a lysate prepared from a mammalian cell line expressing the gene of interest. Effective target sites are identified by performing a primer extension reaction on purified RNA from the lysate using a primer specific for the gene of interest. Primer extension products terminate at the sites of cleavage by effective ribozymes. These sites are identified by gel electrophoresis of the primer extension products with suitable size markers.

EXAMPLE 1

Construction of pASlib. In this example, there is described an illustrative plasmid according to the present invention for making a deletion library of a selected DNA. This plasmid was constructed as follows.

The HindIII-HpaI fragment of pLA2917 (J. N. Allen & R. S. Hanson, 161 J. Bact. 955–962 (1985)), containing the kanamycin resistance gene, was inserted into HindIII/SmaI-digested pUC19 to produce pUCKan. An HphI and two BsaHI sites were eliminated from the kanamycin resistance gene by site-directed mutagenesis, according to methods well known in the art, to produce pUCKan*. The mutagenized kanamycin resistance gene was removed by HindIII/EcoRI digestion, and the termini were blunted by 5'-overhang fill-in using the Klenow fragment of DNA polymerase I and ligated to the 843 bp BspHI-SapI fragment of pUC19 containing the origin of replication. A clone (pKan) was selected wherein the EcoRI and BspHI sites were juxtaposed. The BsmFI and PstI sites were eliminated from pKan by site-directed mutagenesis using the procedure of E. Merino et al., 12 Biotechniques 508–510 (1992). The multiple cloning site for pASlib was constructed from the overlapping oligodeoxynucleotides MCS-L (SEQ ID NO:5) and MCS-R (SEQ ID NO:6) by 5'-overhang fill-in with the Klenow fragment of DNA polymerase I. Oligonucleotides were synthesized using an Applied Biosystems automated oligonucleotide synthesizer. The double-stranded multiple cloning site was inserted into EcoRI-linearized and blunted pKan to result in pASlib (SEQ ID NO:7). Restriction endonuclease digestions, primer extension reactions, ligation reactions, and the like were carried out according to methods well known in the art. E.g., J. Sambrook et al., Molecular Cloning: A Laboratory Manual (2d ed., 1989); T. Maniatis et al., Molecular Cloning: A Laboratory Manual (1982); F. Ausubel et al., Current Protocols in Molecular Biology (1987).

Therefore, pASlib possesses the pUC19 origin of replication and a kanamycin resistance gene allowing selection in bacterial cells. The kanamycin resistance gene was chosen as the selectable marker since, of all the available bacterial selection markers, it possessed the fewest sites present in the MCS. Therefore, it was the simplest to modify by site-specific mutagenesis to eliminate the undesirable sites. The MCS contains the following salient features. It possesses a short polylinker that allows much flexibility in the cloning of the gene or cDNA sequence of interest, which represents the first step in the construction of an antisense library. The polylinker includes several restriction sites that leave sticky ends upon digestion. These sites can be used to directionally clone the cDNA or genomic fragment in the correct orientation. Alternatively, the fragment can be cloned by blunt-end ligation, and the correctly oriented clone can be selected by restriction analysis. The PstI and PmeI sites allow the generation of a substrate for unidirectional digestion by exonuclease III into the cloned cDNA or genomic fragment. This allows preparation of a serial deletion library of the cloned insert. The BsmFI and BbsI sites are used together to convert the deletion library into a 14 bp fragment library. The HphI site allows bisection of the 14 bp fragment library for introduction of the antisense agent.

EXAMPLE 2

Construction of pShuttle. In this example, there is described the construction of an illustrative plasmid for use according to the present invention for expressing an antisense agent in either mammalian cells using the intermediate-early promoter from cytomegalovirus or in vitro using T7 polymerase.

A hygromycin expression cassette capable of being expressed in both mammalian and prokaryotic systems was constructed using overlap extension PCR. PCR was carried out according to methods well known in the art, e.g., U.S. Pat. Nos. 4,683,195; 4,683,202; 4,800,159; 4,965,188; PCR Technology: Principles and Applications for DNA Amplification (H. Erlich ed., Stockton Press, New York, 1989); PCR Protocols: A guide to Methods and Applications (Innis et al. eds, Academic Press, San Diego, Calif., 1990). The 1026 bp hygromycin resistance coding sequence from EBOpLPP (ATCC) was joined at its 3'-end to the 322 bp 3'-untranslated region (UTR)/SV40 early polyadenylation sequence from pRC/CMV (Invitrogen Corp., Carlsbad, Calif.), while the 527 bp dual ampicillin/SV40 early promoter from pEGFP-1 was joined to the 5'-end. The sequences of the primers used in the PCR were as follows: 3'-UTR/poly(A) segment, SEQ ID NO:8 and SEQ ID NO:9; hygromycin coding region, SEQ ID NO:10 and SEQ ID NO:11; amp/SV40 early promoter, SEQ ID NO:12 and SEQ ID NO:13. Each portion of the hygromycin cassette was prepared by PCR using one of the three primer sets and the appropriate template. The resulting fragments were gel purified. The hygromycin-encoding and the 3'-UTR/poly(A) fragments were combined and used in a second PCR reaction to produce the hygromycin-3'-UTR/poly(A) fragment. In a final PCR, this fragment was combined with the amp/SV40 fragment to produce the complete 1875 bp hygromycin gene cassette. The hygromycin gene cassette was ligated into the 843 bp BspHI-SapI oriP-containing fragment of pUC19, producing pHyg. The 4914 bp EcoRI-BamHI fragment containing the EBNA-1 and EBV oriP sequences from EBOpLPP was inserted between the hygromycin cassette and the pUC19 origin of XhoI-digested pHyg to make pEBV. The 1060 bp expression cassette was excised from pRC/CMV using NruI and PvuII and inserted into the BamHI site of pEBV to produce pShuttle (SEQ ID NO: 14).

pShuttle was designed to allow replication and expression of the antisense library in mammalian cells. It possesses an MCS for insertion of the antisense library. The MCS is flanked on one end by a dual CMV/T7 promoter for allowing expression of the antisense agent gene both in mammalian cells as well as by in vitro transcription using T7 RNA polymerase. On the other end of the MCS is a bovine growth hormone polyadenylation signal for efficient expression in mammalian cells. pShuttle possesses a hygromycin resistance gene driven by a dual promoter for allowing selection in bacterial and mammalian cells. The pUC19 origin of replication allows replication in bacterial cells. For replication in mammalian cells, the EBV origin and EBNA-1 gene were included. J. Yates et al., 81 Proc. Nat'l Acad. Sci. USA 3806–3810 (1984); J. Yates et al., 313 Nature 812–815 (1985).

EXAMPLE 3

Construction of a hammerhead ribozyme catalytic core cassette. A cassette encoding the hammerhead catalytic core, interrupted by the CAT gene (S. Horinouchi & B. Weisblum, 150 J. Bact. 815–825 (1982)), was constructed as follows. PCR primers were prepared that were complementary to the CAT gene on their 3'-ends and encoded the hammerhead catalytic core on their 5'-ends. The sequences of the primers were SEQ ID NO:15 and SEQ ID NO:16. Located between the CAT and hammerhead catalytic core sequences were NruI restriction sites. The PCR contained 5 ng CAT gene DNA, 100 pmol each of the primers CatCass 1 and CatCass 2, 1 mM of each of the four dNTPs, 5 units of VENT polymerase (New England Biolabs, Beverly, Mass.) in the standard VENT polymerase buffer except that the concentration of the $MgSO_4$ was increased to 5.2 mM (i.e., 10 mM KCl, 10 mM $(NH_4)_2SO_4$, 20 mM Tris-HCl (pH 8.8 at 24° C.), 5.2 mM $MgSO_4$, 0.1% Triton X-100). The use of VENT polymerase ensured that the cassette possessed blunt ends.

The reaction mixture was incubated as follows:

(A) 2 minutes at 94° C.;

(B) 5 cycles of 1 minute at 94° C., 30 seconds at 45° C., and 2 minutes at 72° C.;

(C) 15 cycles of 30 seconds at 94° C., 15 seconds at 60° C., and 2 minutes at 72° C.; and (D) 5 minutes at 73° C.

After amplification, the cassette was purified from unincorporated primers by agarose gel electrophoresis, and the agarose was subsequently removed from the cassette DNA using standard procedures.

Introduction of a catalytic core into a fragment library presents several difficulties. The core must be inserted by blunt-end ligation and in the correct orientation to produce a functional ribozyme. Additionally, due to its small size, it is difficult to prevent the introduction of concatamers of the core and/or contamination of the library with clones that do not acquire a catalytic core. To increase the effectiveness and efficiency of this step, the core interrupted by the CAT gene was designed. CAT selection allows the use of a non-phosphorylated cassette. This prevents insertion of multimers and selects against non-recombinants. Additionally, the CAT gene allows selection of clones acquiring a correctly oriented catalytic core. In the desired orientation, transcription of the CAT and kanamycin genes is in the same direction. In the incorrect orientation, CAT expression is inhibited by antisense expression from the kanamycin resistance gene. This phenomenon has been noted previously, R. Bruckner et al., 32 Gene 151–1160 (1984). After selection, the CAT gene is removed by digestion with NruI to produce a sequence encoding a hammerhead ribozyme.

EXAMPLE 4

Construction of a Herpes ICP4 ribozyme library. The 4489 bp BglII-EcoRI fragment from pTEG2, X.X. Zhu et al., 184 Virology 67–78 (1991), containing a herpes simplex virus ICP4 genomic fragment was cloned into EcoRI-EcoRV-digested pASlib. This fragment included 125 bp upstream of the translational start site, 466 bp downstream of the translational termination sequence, and the entire genomic coding sequence of ICP4. The resulting clone, pASlib-ICP4, contained the ICP4 fragment with the sense strand as the upper strand.

From pASlib-ICP4 a deletion library was produced as follows. Twenty µg of CsCl gradient purified plasmid DNA was digested with PstI and XbaI, then concentrated and desalted using a Microcon 50 spin filter (Amicon). The DNA was brought up to a volume of 60.4 µl of exonuclease III buffer (i.e., 50 mM Tris-HCl, pH 8.0, 5 mM MgCl2, 10 mM 2-mercaptoethanol), warmed to 37° C., and then 300 units of exonuclease III were added. At 1-minute intervals after the addition of the exonuclease III, 2.5 µl of the reaction mixture was removed and placed in microfuge tubes on ice containing 7.5 µl of 66.7 mM sodium acetate, pH 5.2, 200 mM NaCl, 1.3 mM $ZnCl_2$, and 1 unit of mung bean nuclease. After 25 aliquots had been removed, the mung bean nuclease-containing tubes were incubated at 20° C. for 30 minutes. After 30 minutes, the contents of all of the mung bean nuclease-containing tubes were combined and extracted with phenol-chloroform (50:50), extracted with chloroform, and then were precipitated with two volumes of 100% ethanol. The DNA was then pelleted and dried. The DNA was then resuspended in 18 µl of d.i. $H_2O$, 2.5 µl of 10 mM of each of the four dNTPs, 2.5 µl of 10×Pfu polymerase buffer (e.g., 100 mM KCl, 100 mM $(NH_4)_2SO_4$, 200 mM Tris-Cl (pH 8.75), 20 mM $MgSO_4$, 1% Triton® X-100, 1000 mg/ml BSA), and 5 units of Pfu polymerase (Stratagene, La. Jolla, Calif.), then incubated at 72° C. for 15 minutes, and cooled to room temperature. The plasmid DNA was recircularized by ligating in a large volume (1.25 ml) in a buffer containing 5% PEG for 4 hours at room temperature. Except for the modifications indicated, all ligations were performed with T4 DNA ligase under the conditions suggested by the manufacturer.

After transformation into *E. coli* DH5α, the cells were grown in liquid culture to amplify the deletion library. The library DNA was purified and digested with BsmFI and BbsI, and then the ends were blunted with Pfu polymerase as described above. The DNA was then recircularized by ligation in a 600 µl volume in a buffer containing 5% polyethylene glycol (PEG) at room temperature for 4 hours. After transformation into *E. coli* DH5α, amplification and plasmid purification, 1 µg of library plasmid DNA was then subjected to digestion with 8 units of HphI for 1 hour at 37° C., and the ends were polished with T4 DNA polymerase. The hammerhead core cassette was inserted by ligating 0.5 µg of the HphI-digested library DNA with 5 µg of the ribozyme core sequence cassette prepared according to the procedure of Example 3. That ligation product was transformed into DH5α and grown in culture under chloramphenicol selection. After purification, 2 µg of the DNA was digested with HindIII and SalI, and the terminal phosphates were removed using shrimp alkaline phosphatase (Amersham, Arlington Heights, Ill.). The HindIII/SalI digest was fractionated on an agarose gel, and the dephosphorylated ribozyme/chloramphenicol cassette was purified using standard procedures. The cassette was combined with an equimolar amount of HindIII-XhoI-digested pShuttle, prepared according to the procedure of Example 2, and ligated using a modified two-step ligation procedure, S. Damak & D. W. Bullock, 15 Biotechniques 448–450 (1993) (hereby incorporated by reference). The first step was performed at room temperature for 1 hour, and the second step was incubated overnight at 16° C. The ligation mixture was transformed in DH5α and grown in culture under chloramphenicol selection. The library DNA was purified and then digested with NruI to release the chloramphenicol gene. The digested DNA was then recircularized by ligation in a volume of 600 µl. The final ligation product was transformed into DH5α, and the plasmid DNA was purified on a CsCl gradient.

To verify the effectiveness of this procedure, 56 clones obtained at various steps were sequenced. Thirty-one were from the final ribozyme library, and the remainder were from earlier steps, beginning with the 14 bp fragment library. The results of the sequencing are discussed below.

One observation made after the mung bean digestion was that the deletions infrequently stopped at A-T base pairs. While exonuclease III has been shown to exhibit a preference for stopping at certain nucleotides (C>A=T>G), W. Linxweiler & W. Horz, 10 Nucleic Acids Res. 4845–4859 (1982), this was not believed to be the cause of the observed sequence bias. Instead, it is believed that this is the result of a greater degree of "breathing" at A-T terminated deletions and the subsequent removal of A-T terminal pairs by mung bean nuclease. The mung bean nuclease digestion was later performed at higher salt concentrations (150 mM) and at a lower temperature (20° C.). This eliminated the under-representation of A-T terminated deletions.

For construction of the library, two type IIS restriction enzymes are required, BsmFI and HphI. Typical of type IIS restriction enzymes, BsmFI and HphI cleave downstream of their recognition sequences in a sequence-independent manner. Cleavage by type IIS restriction enzymes can pose some problems since they can exhibit infidelity in how far from their recognition site they cleave. Cleavage by BsmFI was largely at the expected distance (10/14), but also at 11/15. The reported 9/13 activity for this enzyme, V. E. Velculescu et al., 270 Science 484–487 (1995), was not seen in any of the clones sequenced. Infidelity of BsmFI does not present a problem for construction of ribozyme libraries. The result of this infidelity is that the recognition domains of the ribozymes in the library can vary from 13 to 15 nucleotides.

Figure 1B:
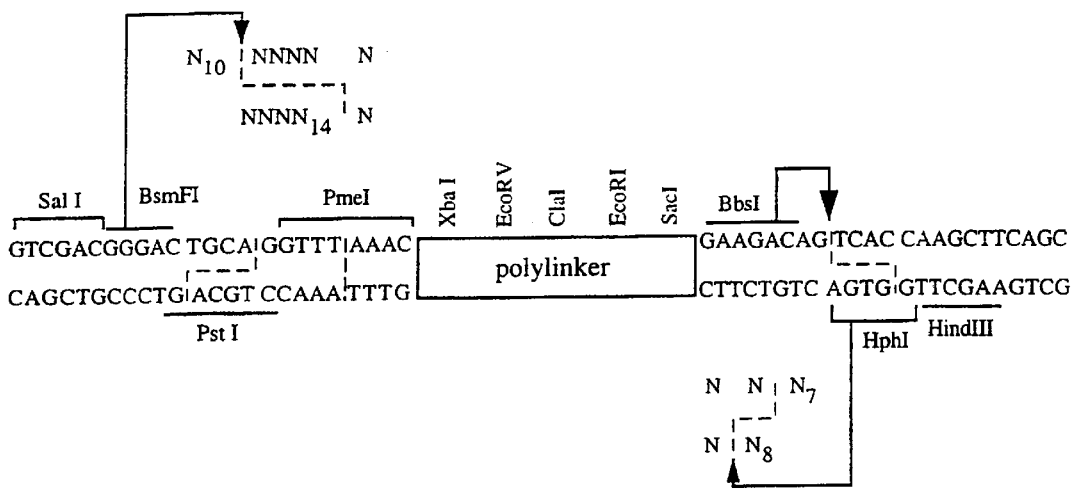

In contrast, HphI infidelity can be problematical. HphI digestion is a critical step in the construction of ribozyme libraries. This enzyme produces a 1 nucleotide 3'-overhang that is later removed by polishing with T4 DNA polymerase. It is essential to the proper functioning of the resulting ribozyme that this 1 nucleotide be removed, since it does not have an antisense binding partner in the ribozyme (FIG. 1, X).

HphI cleaves at 8/7, but also at 9/8. D. Kleid et al., 73 Proc. Nat'l Acad. Sci. USA 293–297 (1976). This infidelity is demonstrated in the present library by the presence of ribozymes with flanking helices of length 8 and 5, as would be expected if HphI cleaved at 9/8. This type of infidelity, in itself, is not problematical. It simply alters the relative lengths of the two arms of the binding domain, leaving the total length of the binding arms unchanged. The problem that arises with HphI infidelity is that the enzyme can cleave twice at the same target, i.e., if it first cleaves at 9/8 it can rebind and cleave at 8/7. The result is that 2 bp are removed from the sequence upon polishing with T4 DNA polymerase. Removal of 2 bp from the insertion site of the ribozyme core produces a non-functional ribozyme. In early attempts to produce a library, >40% of the clones were the product of double cutting. This is close to the statistically predicted 50% that would occur if HphI has no preference for either 8/7 or 9/8 cutting. To minimize the possibility of double cutting, HphI digestion was performed under near "single hit" conditions. Under these conditions, double cleavage was only 13% of the final library. It should be possible to further reduce the percentage of double hits by performing the cleavage under "sub-single hit" conditions. This should not present any problem so long as the amount of plasmid digested is sufficient to allow full representation of the ribozyme library. Undigested molecules cannot accept the catalytic core and are removed in the later step by selection for chloramphenicol resistance. Other class IIS restriction enzymes, such as MboII, could likely substitute for HphI, but fidelity may not be any better.

The infidelity of HphI raises another issue. It is possible that some sequences favor digestion at 8/7 and others at 9/8. This could lead to the absence of some ribozyme target sequences in the final library. This appears to be unlikely, however. First, as discussed, under conditions that give nearly 100% cleavage by HphI, >40% of the molecules are cut twice. This is close to the 50% predicted if HphI exhibits no preference for 8/7versus 9/8 cutting. Second, two clones that both contain the same 14 bp sequence of ICP4, Rz8 and Rz9 (Table 1), are the products of 8/7 and 9/8 cleavage, respectively. This suggests that the intervening sequence between the binding site and the cleavage site does not affect where HphI cleaves.

HphI is also sensitive to overlapping dam methylation. This is also true of MboII. Since 2 nucleotides of the four base consensus sequence for darn methylation are provided by the variable sequence of the cDNA insert, mathematically 1/16 of the clones in the 14 bp fragment library (6.25%) will not be cleaved with HphI and will be eliminated from the final ribozyme library. This can be prevented by passage of the 14 bp fragment library in a dam_ strain prior to HphI digestion.

TABLE 1

| Clone (Position) | Target Sequence[a] | SEQ ID NO: |
|---|---|---|
| Rz1 (1754) | cgacgccgcccgcc | 19 |
| Rz2 (1992) | cugcgcgcguggcu | 20 |
| Rz3 (2045) | gcgccugcgcgggg | 21 |
| Rz4 (2252) | cgccgccgacgcgc | 22 |
| Rz5 (2411) | cccccuccccgcg | 23 |
| Rz6 (2517) | guggcccugucgcg | 24 |
| Rz7 (2590) | gccacacggcggcg | 25 |
| Rz8 (2729) | cgccgcgcggugcg | 26 |
| Rz9 (2729)[b] | cgccgcgcggugcg | 27 |
| Rz10 (2837) | cccccugcgcgccuc | 28 |
| Rz11 (2915) | gguggugcuguacuc | 29 |
| Rz12 (3246) | gggcccgcgguguc | 30 |
| Rz13 (3275)[c] | ccuggcgugcgagc | 31 |
| Rz14 (3569) | ggggaccaccgacgccauggc | 32 |
| Rz15 (3680) | cguggcgcuggggc | 33 |
| Rz16 (3842) | cgggauucgcuggg[d] | 34 |

[a]The nucleotide in bold indicates the unbound nucleotide, i.e., position X in FIG. 3.
[b]Clone repeated 2 times.
[c]Clone repcated 3 times.
[d]Bona fide ribozyme target.

Figure 8:
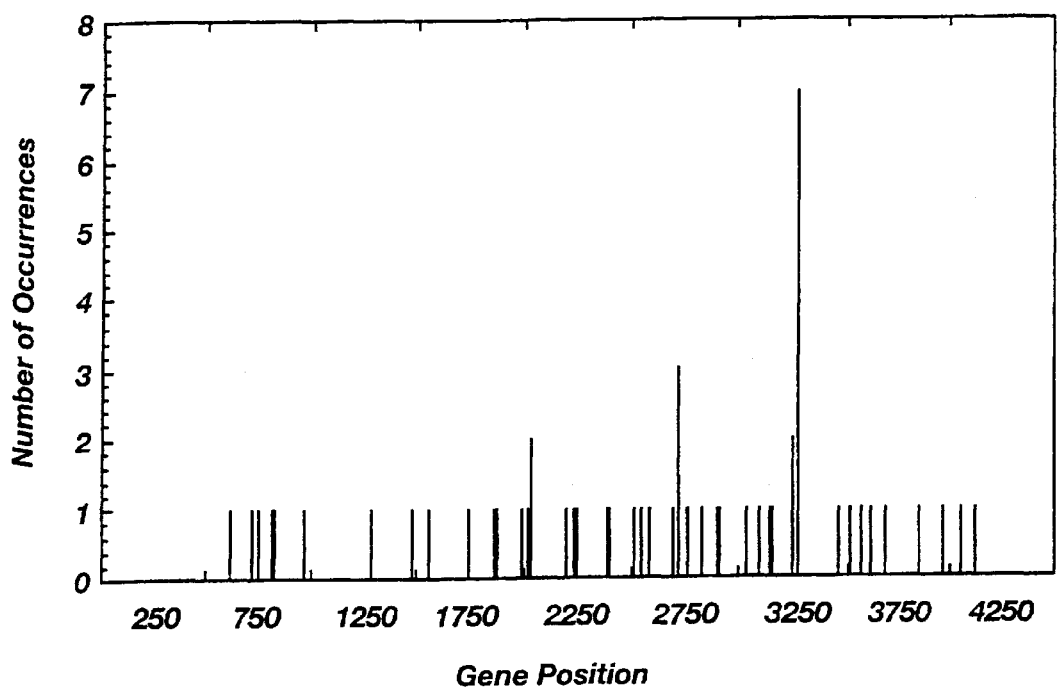
FIG. 8 shows a histogram of the distribution of 56 target sites in an illustrative antisense library according to the present invention.

The target locations of the 56 sequenced clones are illustrated in FIG. 8. The histogram indicates that the target sites are fairly evenly distributed across the entire ICP4 gene, with the exception that no clones were identified targeting the 5'- and 3'-termini. It is unlikely that the library is devoid of members targeting these regions since the libraries are prepared with complexities far exceeding the total number of sites on the gene. It is even possible that target sites in these regions are similarly represented as those identified by the sequenced clones. Due to the small number of clones sequenced, it is likely that some larger gaps in the data could be observed even for a uniformly represented library, such as the gap between positions 966 and 1282.

Of the 56 sequences determined, 42 (75%) occurred only once, while four occurred multiple times (FIG. 8). Three were only mildly over-represented, with two or three occurrences compared with the single occurrence for the majority of clones. The three positions were 2054 and 3246, with two occurrences each, and position 2729, with three occurrences. One position, 3275, was significantly over-represented, occurring seven times. Five of the occurrences were observed within the 32 clones sequenced from the final library, and the other two were found at early stages of the construction. The over-representation of particular sites is likely caused by some local sequence and/or structure in the DNA that either stalls exonuclease m or causes it to fall off the template. P. Abarzua & K. J. Marians, 81 Proc. Nat'l Acad. Sci. USA 2030–2034 (1984). Performing the exonuclease III deletion at higher temperatures might reduce this phenomenon if an inhibitory structure is forming at certain sequences. Higher temperature also allows for more distributive activity from the enzyme, J. D. Hoheisel, 209 Anal. Biochem. 238–246 (1993), which is desirable in this type of exonuclease III digestion. While it is possible that the exonuclease III digestion conditions may need to be optimized for each target cDNA, creating libraries larger than would be necessary to represent every position would ensure complete representation of all target sites.

Examination of the 31 clones obtained from the final library allowed determination of the overall effectiveness of the procedure. All 31 possessed a catalytic core, demonstrating the effectiveness of the use of CAT selection for this purpose. Nineteen of the 31 clones *\(61%) contained sequences that could potentially be ribozymes if the sequence that they targeted included the required NUH sequence at the correct location. These are shown in Table 1. Counted among these potential ribozymes were three clones that possess non-detrimental defects. One has a single nucleotide deleted from loop II of the ribozyme (Rz13). This produces a three-, instead of a four-nucleotide loop II. The site of this defect is the NruI site used to remove CAT from the catalytic core. The ends must have been damaged during this step for this clone. The other two non-detrimental defects were the result of incomplete digestion by BsmFI. These clones have a longer flanking arm corresponding to helix III (Rz12 and Rz14). This appears to be the result of a lack of cleavage of the BsmFI site on pASlib and, instead, an internal BsmFI site on ICP4 was used. These clones would be expected to produce functional ribozymes had they targeted an NUH sequence.

The remaining 12 clones (39% of 31) possessed defects that would prevent them from being potentially functional ribozymes. Four of these (13%) were defective in that they were cleaved twice with HphI. As discussed above, it is likely that this defect can be reduced to close to zero by performing the HphI digestion under "sub-single hit" conditions. Three (9.7%) were missing 1 nucleotide from one end of the catalytic core. Since the deletion always occurred at the same end of the cassette and the thermostable polymerase used to make the cassette does not contain any 5' to 3' exonuclease activity, the PCR primer constituting that end of the cassette must have been contaminated with a small percentage of a failure fragment of the DNA synthesis. This defect can be eliminated by better purification of the primers. Five clones (16%) possessed the catalytic core in the incorrect orientation. This is in contrast to the expected 50% if there were no selection for orientation. Incorrectly oriented clones could be eliminated by moving the promoter for the CAT gene outside the MCS of pASlib. Finally, three clones were the result of various unknown cloning artifacts.

Therefore, the success rate of this library was 61%. As discussed, a few procedural changes would increase the success rate to 70–80%. This could be increased a further 16% by placing the CAT promoter outside the MCS. Even at 61%, the success rate is more than adequate. This just means that it is necessary to screen an antisense library 140% the size needed if 100% success were achieved. This would still be a small library relative to a non-directed library approach.

Three of the 31 clones (9.7%) targeted a site on the ICP4 mRNA that contained a uridine at the proper position of the consensus NUH site (Rz3, Rz5, and Rz16). Of the three, only one targeted a consensus NUH site (Rz16). Due to the unusually high G/C content of the ICP4 genomic fragment used to make the ribozyme library, only 9.2% of the nucleotides in the mRNA are uridines, of which 203 occur as an NUH triplet. The fact that the percentage of sequenced clones in the library targeting an NU site is virtually identical to the percentage of uridines in the ICP4 gene suggests that the library is unbiased and likely to contain a fairly uniform distribution of target sites.

The use of a direct library for target site selection significantly simplifies the screening process, since only very small libraries need be prepared and assayed. For ICP4, assuming the library contains a uniform distribution of the 4475 distinct sequences (4489-14), a library of 67,125 (15-fold excess) is expected to have a probability of 99.9% of containing all sequences. W. Feller, An Introduction to Probability Theory and Its Applications (3d ed. 1968). Based on a $\chi^2$ goodness-of-fit analysis of the 56 sequences, the multiples observed at positions 2729 and 3275 occur with a higher frequency than would be expected for a uniform distribution. All other positions are consistent with a uniform distribution. Correcting for the two over-represented sequences, a library of 81,057 (18-fold excess) is expected to contain all sequences with probability of 99.9%. Preparation, manipulation, and screening of such a library is well within the limitations of current practice. In contrast, a non-directed library targeting 14 nucleotides would require a minimum size of $2.7 \times 10^8$ ($4^{14}$). The ability to prepare and screen such a library is questionable. Even if possible, the vast majority of members of the library are directed at non-target genes. Inhibition of non-target genes could pose problems in interpreting the results.

We claim:

1. A method for generating an oligonucleotide library targeted to a selected RNA transcript comprising:
   (a) preparing a double stranded cDNA, comprising a first end, a second end, and a central site thereof, from the selected RNA transcript and cloning the cDNA in a cloning vector comprising a promoter configured such that an antisense transcript of the cDNA is synthesized upon transcription mediated by the promoter, resulting in a cloned cDNA;
   (b) creating a plurality of deletion derivatives of said cloned cDNA by exonuclease resection thereof, wherein each of said plurality of deletion derivatives has a deletion extending from said first end towards the central site of the cloned cDNA such that the plurality of deletion derivatives comprises a deletion library comprising deletions that extend serially into the cDNA; and
   (c) reducing the size of the cDNA contained in the deletion library to a preselected size by removing a portion of the cDNA from the second end thereof to result in a fragment library;
   (d) inserting a catalytic core into the central site of the cDNA in the fragment library, thereby obtaining the oligonucleotide library.

2. The method of claim 1 wherein said cloning vector comprises a multi-cloning sequence represented by SEQ ID NO:1.

3. The method of claim 1 wherein said plurality of deletion derivatives is created with exonuclease III resection of the cloned cDNA.

4. The method of claim 1 wherein said reducing the size of the cDNA contained in the deletion library to a preselected size comprises digesting the deletion library with a type IIS restriction endonuclease.

5. The method of claim 1 wherein said inserting a catalytic core into the central site of the cDNA in the fragment library comprises digesting the fragment library with a type IIs restriction endonuclease, thereby creating said central site, and ligating the catalytic core at the central site.

6. The method of claim 1 wherein said catalytic core comprises a ribozyme catalytic core.

7. The method of claim 1 wherein said catalytic core is a hammerhead ribozyme catalytic core.

8. A multi-cloning sequence represented by SEQ ID NO:1.

* * * * *

UNITED STATES PATENT AND TRADEMARK OFFICE
CERTIFICATE OF CORRECTION

PATENT NO. : 6,586,180 B1
DATED : July 1, 2003
INVENTOR(S) : Duane E. Ruffner et al.

It is certified that error appears in the above-identified patent and that said Letters Patent is hereby corrected as shown below:

Title page,
Item [56], References Cited, U.S. PATENT DOCUMENTS,
"5,496,698 A * 3/1996 Draper et al. ……………….. 435/6" should read
-- 5,496,698 A * 3/1996 Draper et al. …………………..435/6
  5,525,468 A  6/1996  McSwiggen……………………..435/6 --
OTHER PUBLICATIONS, "Hasan et al., Gene (1986) 50: 55-62.*" should read
-- Hasan et al., Gene (1986) 50:55-62.*
Pierce et al., Construction of a directed hammerhead ribozyme library: towards the identification of optimal target sites for antisense-mediated gene inhibition, 26 Nucleic Acids Research 5093-5101 (1998).
Matveeva et al., A rapid in vitro method for obtaining RNA accessibility patterns for complementary DNA probes: correlation with an itracellular pattern an know RNA structures, 25 Nucleic Acids Research 5010-5016 (1997). --

Signed and Sealed this

Twenty-eighth Day of September, 2004

JON W. DUDAS
*Director of the United States Patent and Trademark Office*

SEQUENCE LISTING

<160> NUMBER OF SEQ ID NOS: 50

<210> SEQ ID NO 1
<211> LENGTH: 62
<212> TYPE: DNA
<213> ORGANISM: Artificial Sequence
<220> FEATURE:
<223> OTHER INFORMATION: Multiple cloning site for use in making deletion libraries.

<400> SEQUENCE: 1
gcttggtgat gcattcgata tcgtttaaac gcccgggcgc ggccgcggcg        50
cctccagtcg ac        62

<210> SEQ ID NO 2
<211> LENGTH: 24
<212> TYPE: DNA
<213> ORGANISM: Artificial Sequence
<220> FEATURE:
<223> OTHER INFORMATION: Portion of a multiple cloning site for use in making deletion libraries.

<400> SEQUENCE: 2
gtcgacggga ctgcaggttt aaac        24

<210> SEQ ID NO 3
<211> LENGTH: 23
<212> TYPE: DNA
<213> ORGANISM: Artificial Sequence
<220> FEATURE:
<223> OTHER INFORMATION: Portion of a multiple cloning site for use in making deletion libraries.

<400> SEQUENCE: 3
gaagacagtc accaagcttc agc        23

<210> SEQ ID NO 4
<211> LENGTH: 23
<212> TYPE: DNA
<213> ORGANISM: Unknown
<220> FEATURE:
<223> OTHER INFORMATION: Catalytic core of hammerhead ribozyme.

<400> SEQUENCE: 4
ctgatgaggt cgcgagaccg aaa        23

<210> SEQ ID NO 5
<211> LENGTH: 49
<212> TYPE: DNA

<213> ORGANISM: Artificial Sequence
<220> FEATURE:
<223> OTHER INFORMATION: PCR primer for construction of pASlib.

<400> SEQUENCE: 5
aagcttggtg actgtcttcg agctcgaatt catcgatatc tagagttta          49

<210> SEQ ID NO 6
<211> LENGTH: 34
<212> TYPE: DNA
<213> ORGANISM: Artificial Sequence
<220> FEATURE:
<223> OTHER INFORMATION: PCR primer for construction of pASlib.

<400> SEQUENCE: 6
gtcgacggga ctgcaggttt aaactctaga tatc                          34

<210> SEQ ID NO 7
<211> LENGTH: 2077
<212> TYPE: DNA
<213> ORGANISM: Artificial Sequence
<220> FEATURE:
<223> OTHER INFORMATION: pASlib

<400> SEQUENCE: 7

| | |
|---|---|
| tcagtggaac gaaaactcac gttaagggat tttggtcatg aattgtcgac | 50 |
| gggactgcag gtttaaactc tagatatcga tgaattcgag ctcgaagaca | 100 |
| gtcaccaagc ttattcccag agtcacgctc agaagaactc gtcaagaagg | 150 |
| cgatagaagg cgatgcgctg cgaatcggga gcggcgatac cgtaaagcac | 200 |
| gaggaagcgg tcagcccatt cgccgccaag ctcttcagca atatcacggg | 250 |
| tagccaacgc tatgtcctga tagcggtccg ccacacccag ccggccacag | 300 |
| tcgatgaatc cagaaaagcg gccattttcc accatgatat tcggcaagca | 350 |
| ggcatcgcca tgggtcacga cgagatcctc gccgtcgggc atgcgcgcct | 400 |
| tgagcctggc gaacagttcg gctggcgcga gcccctgatg ctcttcgtcc | 450 |
| agatcatcct gatcgacaag accggcttcc atccgagtac gtgctcgctc | 500 |
| gatgcgatgt ttcgcttggt ggtcgaatgg gcaggtagcc ggatcaagcg | 550 |
| tatgcagccg ccgcattgca tcagccatga tggatacttt ctcggcagga | 600 |
| gcaagatgag atgacaggag atcctgcccc ggcacttcgc ccaatagcag | 650 |
| ccaatccctt cccgcttcag tgacaacgtc gagcacagct gcgcaaggaa | 700 |
| cgcccgtcgt ggcaagccac gatagccgcg ctgcctcgtc ttgcagttca | 750 |
| ttcagggcac cggacaggtc ggtcttgaca aaaagaaccg gcgcccctg | 800 |
| cgctgacagc cggaacacgg cggcatcaga ggagccgatt gtctgttgtg | 850 |
| cccagtcata gccgaatagc ctctccaccc aagcggccgg agaacctgcg | 900 |
| tgcaatccat cttgttcaat catgcgaaac gatcctcatc ctgtctcttg | 950 |
| atcagatctt gatccctgc gccatcagat ccttggcggc aagaaagcca | 1000 |
| tccagtttac tttgcagggc ttcccaacct taccagaggt cgccccagct | 1050 |
| ggcaattccg gttcgcttgc tgtccataaa accgcccagt ctagctatcg | 1100 |
| ccatgtaagc ccactgcaag ctacctgctt tctctttgcg cttgcgtttt | 1150 |
| cccttgtcca gatagcccag tagtgacatt catccggggt cagcaccgtt | 1200 |
| tctgcggact ggctttctac gtgttccgct tcctttagca gcccttgcgc | 1250 |

```
cctgagtgct tgcggcagcg tgaagctgct tcctcgctca ctgactcgct            1300
gcgctcggtc gttcggctgc ggcgagcggt atcagctcac tcaaaggcgg            1350
taatacggtt atccacagaa tcaggggata acgcaggaaa gaacatgtga            1400
gcaaaaggcc agcaaaaggc caggaaccgt aaaaaggccg cgttgctggc            1450 gttttccat aggctccgcc cccctgacga gcatcacaaa aatcgacgct             1500
caagtcagag gtggcgaaac ccgacaggac tataaagata ccaggcgttt            1550
ccccctggaa gctccctcgt gcgctctcct gttccgaccc tgccgcttac            1600
cggatacctg tccgcctttc tcccttcggg aagcgtggcg ctttctcaat            1650
gctcacgctg taggtatctc agttcggtgt aggtcgttcg ctccaagctg            1700
ggctgtgtgc acgaaccccc cgttcagccc gaccgctgcg ccttatccgg            1750
taactatcgt cttgagtcca acccggtaag cacgacttat cgccactgg             1800 cagcagccac tggtaacagg attagcagag cgaggtatgt aggcggtgct            1850
acagagttct tgaagtggtg gcctaactac ggctacacta gaaggacagt            1900
atttggtatc tgcgctctgc tgaagccagt taccttcgga aaaagagttg            1950
gtagctcttg atccggcaaa caaaccaccg ctggtagcgg tggtttttt             2000 gtttgcaagc agcagattac gcgcagaaaa aaaggatctc aagaagatcc            2050
tttgatcttt tctacgggt ctgacgc                                      2077
```

```
<210> SEQ ID NO 8
<211> LENGTH: 33
<212> TYPE: DNA
<213> ORGANISM: Artificial Sequence
<220> FEATURE:
<223> OTHER INFORMATION: PCR primer for amplifying a 3'-UTR/poly(A)
      segment.

<400> SEQUENCE: 8
ccgagggcaa aggataggc gggactctgg ggt                               33

<210> SEQ ID NO 9
<211> LENGTH: 21
<212> TYPE: DNA
<213> ORGANISM: Artificial Sequence
<220> FEATURE:
<223> OTHER INFORMATION: PCR primer for amplifying a 3'-UTR/poly(A)
      segment.

<400> SEQUENCE: 9
ctcgaggtcg acgggatcca g                                           21

<210> SEQ ID NO 10
<211> LENGTH: 33
<212> TYPE: DNA
<213> ORGANISM: Artificial Sequence
<220> FEATURE:
<223> OTHER INFORMATION: PCR primer for amplifying a hygromycin coding
      region.

<400> SEQUENCE: 10
ggatgaggat cgtttcgcat gaaaaagcct gaa                              33

<210> SEQ ID NO 11
<211> LENGTH: 33
<212> TYPE: DNA
<213> ORGANISM: Artificial Sequence
```

```
<220> FEATURE:
<223> OTHER INFORMATION: PCR primer for amplifying a hygromycin coding
      region.

<400> SEQUENCE: 11
accccagagt cccgcctatt cctttgccct cgg                              33

<210> SEQ ID NO 12
<211> LENGTH: 20
<212> TYPE: DNA
<213> ORGANISM: Artificial Sequence
<220> FEATURE:
<223> OTHER INFORMATION: PCR primer for amplifying an amp/SV40 early
      promoter.

<400> SEQUENCE: 12
cgtcaggtgg cacttttcgg                                             20

<210> SEQ ID NO 13
<211> LENGTH: 33
<212> TYPE: DNA
<213> ORGANISM: Artificial Sequence
<220> FEATURE:
<223> OTHER INFORMATION: PCR primer for amplifying the amp/SV40 early
      promoter.

<400> SEQUENCE: 13
ttcaggcttt ttcatgcgaa acgatcctca tcc                              33

<210> SEQ ID NO 14
<211> LENGTH: 8705
<212> TYPE: DNA
<213> ORGANISM: Artificial Sequence
<220> FEATURE:
<223> OTHER INFORMATION: pShuttle

<400> SEQUENCE: 14
tcgagcatga ccaaaatccc ttaacgtgag ttttcgttcc actgagcgtc            50
agaccccgta gaaaagatca aaggatcttc ttgagatcct ttttttctgc           100
gcgtaatctg ctgcttgcaa acaaaaaaac caccgctacc agcggtggtt           150
tgtttgccgg atcaagagct accaactctt tttccgaagg taactggctt           200
cagcagagcg cagataccaa atactgtcct tctagtgtag ccgtagttag           250
gccaccactt caagaactct gtagcaccgc ctacatacct cgctctgcta           300
atcctgttac cagtggctgc tgccagtggc gataagtcgt gtcttaccgg           350
gttggactca agacgatagt taccggataa ggcgcagcgg tcgggctgaa           400
cggggggttc gtgcacacag cccagcttgg agcgaacgac ctacaccgaa           450
ctgagatacc tacagcgtga gcattgagaa agcgccacgc ttcccgaagg           500
gagaaaggcg gacaggtatc cggtaagcgg cagggtcgga acaggagagc           550
gcacgaggga gcttccaggg ggaaacgcct ggtatcttta tagtcctgtc           600
gggtttcgcc acctctgact tgagcgtcga ttttgtgat gctcgtcagg           650 ggggcggagc ctatggaaaa acgccagcaa cgcggccttt ttacggttcc           700
tggccttttg ctggcctttt gctcacatgt tctttcctgc gttatcccct           750
gattctgtgg ataaccgtat taccgccttt gagtgagctg ataccgctcg           800
ccgcagccga acgaccgagc gcagcgagtc agtgagcgag gaagccgtca           850
ggtggcactt ttcggggaaa tgtgcgcgga accctatttt gtttattttt          900
```

-continued

```
ctaaatacat tcaaatatgt atccgctcat gagacaataa ccctgataaa        950
tgcttcaata atattgaaaa aggaagagtc ctgaggcgga aagaaccagc       1000
tgtggaatgt gtgtcagtta gggtgtggaa agtccccagg ctccccagca       1050
ggcagaagta tgcaaagcat gcatctcaat tagtcagcaa ccaggtgtgg       1100
aaagtcccca ggctccccag caggcagaag tatgcaaagc atgcatctca       1150
attagtcagc aaccatagtc cgcccctaa ctccgcccat cccgcccta         1200
actccgccca gttccgccca ttctccgccc catggctgac taatttttt        1250
tatttatgca gaggccgagg ccgcctcggc ctctgagcta ttccagaagt       1300
agtgaggagg ctttttggga ggcctaggct tttgcaaaga tcgatcaaga       1350
gacaggatga ggatcgtttc gcatgaaaaa gcctgaactc accgcgacgt       1400
ctgtcgagaa gtttctgatc gaaaagttcg acagcgtctc cgacctgatg       1450
cagctctcgg agggcgaaga atctcgtgct ttcagcttcg atgtaggagg       1500
gcgtggatat gtcctgcggg taaatagctg cgccgatggt ttctacaaag       1550
atcgttatgt ttatcggcac tttgcatcgg ccgcgctccc gattccggaa       1600
gtgcttgaca ttggggaatt cagcgagagc ctgacctatt gcatctcccg       1650
ccgtgcacag ggtgtcacgt tgcaagacct gcctgaaacc gaactgcccg       1700
ctgttctgca gccggtcgcg gaggccatgg atgcgatcgc tgcggccgat       1750
cttagccaga cgagcgggtt cggcccattc ggaccgcaag gaatcggtca       1800
atacactaca tggcgtgatt tcatatgcgc gattgctgat ccccatgtgt       1850
atcactggca aactgtgatg gacgacaccg tcagtgcgtc cgtcgcgcag       1900
gctctcgatg agctgatgct ttgggccgag gactgccccg aagtccggca       1950
cctcgtgcac gcggatttcg gctccaacaa tgtcctgacg gacaatggcc       2000
gcataacagc ggtcattgac tggagcgagg cgatgttcgg ggattcccaa       2050
tacgaggtcg ccaacatctt cttctggagg ccgtggttgg cttgtatgga       2100
gcagcagacg cgctacttcg agcggaggca tccggagctt gcaggatcgc       2150
cgcggctccg ggcgtatatg ctccgcattg gtcttgacca actctatcag       2200
agcttggttg acggcaattt cgatgatgca gcttgggcgc agggtcgatg       2250
cgacgcaatc gtccgatccg gagccgggac tgtcgggcgt acacaaatcg       2300
cccgcagaag cgcggccgtc tggaccgatg gctgtgtaga agtactcgcc       2350
gatagtggaa accgacgccc cagcactcgt ccgagggcaa aggaataggc       2400
gggactctgg ggttcgaaat gaccgaccaa gcgacgccca acctgccatc       2450
acgagatttc gattccaccg ccgccttcta tgaaaggttg gcttcggaa        2500
tcgttttccg ggacgccggc tggatgatcc tccagcgcgg ggatctcatg       2550
ctggagttct tcgcccaccc caacttgttt attgcagctt ataatggtta       2600
caaataaagc aatagcatca caaatttcac aaataaagca tttttttcac       2650
tgcattctag ttgtggtttg tccaaactca tcaatgtatc ttatcatgtc       2700
tggatccgat gtacgggcca gatatacgcg ttgacattga ttattgacta       2750
gttattaata gtaatcaatt acgggtcat tagttcatag cccatatatg        2800
gagttccgcg ttacataact tacggtaaat ggcccgcctg gctgaccgcc       2850
```

-continued

| | |
|---|---|
| caacgaccccc cgcccattga cgtcaataat gacgtatgtt cccatagtaa | 2900 |
| cgccaatagg gactttccat tgacgtcaat gggtggacta tttacggtaa | 2950 |
| actgcccact tggcagtaca tcaagtgtat catatgccaa gtacgccccc | 3000 |
| tattgacgtc aatgacggta aatggcccgc ctggcattat gcccagtaca | 3050 |
| tgaccttatg ggactttcct acttggcagt acatctacgt attagtcatc | 3100 |
| gctattacca tggtgatgcg gttttggcag tacatcaatg ggcgtggata | 3150 |
| gcggtttgac tcacggggat ttccaagtct ccaccccatt gacgtcaatg | 3200 |
| ggagtttgtt ttggcaccaa aatcaacggg actttccaaa atgtcgtaac | 3250 |
| aactccgccc cattgacgca aatgggcggt aggcgtgtac ggtgggaggt | 3300 |
| ctatataagc agagctctct ggctaactag agaacccact gcttaactgg | 3350 |
| cttatcgaaa ttaatacgac tcactatagg gagacccaag cttggtaccg | 3400 |
| agctcggatc cactagtaac ggccgccagt gtgctggaat tctgcagata | 3450 |
| tccatcacac tggcggccgc tcgagcatgc atctagaggg ccctattcta | 3500 |
| tagtgtcacc taaatgctag agctcgctga tcagcctcga ctgtgccttc | 3550 |
| tagttgccag ccatctgttg tttgcccctc ccccgtgcct tccttgaccc | 3600 |
| tggaaggtgc cactcccact gtcctttcct aataaaatga ggaaattgca | 3650 |
| tcgcattgtc tgagtaggtg tcattctatt ctggggggtg gggtggggca | 3700 |
| ggacagcaag ggggaggatt gggaagacaa tagcaggcat gctggggatg | 3750 |
| cggtgggctc tatggcttct gaggcggaaa gaaccaggat cccccgccgc | 3800 |
| cggacgaact aaacctgact acggcatctc tgccccttct tcgctggtac | 3850 |
| gaggagcgct tttgttttgt attggtcacg gggcagtgca tgtaatccct | 3900 |
| tcagttggtt ggtacaactt gccaactggg ccctgttcca catgtgacac | 3950 |
| ggggggggac caaacacaaa ggggttctct gactgtagtt gacatcctta | 4000 |
| taaatggatg tgcacatttg ccaacactga gtggctttca tcctggagca | 4050 |
| gactttgcag tctgtggact gcaacacaac attgccttta tgtgtaactc | 4100 |
| ttggctgaag ctcttacacc aatgctgggg gacatgtacc tcccaggggc | 4150 |
| ccaggaagac tacgggaggc tacaccaacg tcaatcagag gggcctgtgt | 4200 |
| agctaccgat aagcggaccc tcaagagggc attagcaata gtgtttataa | 4250 |
| ggccccccttg ttaaccctaa acgggtagca tatgcttccc gggtagtagt | 4300 |
| atatactatc cagactaacc ctaattcaat agcatatgtt acccaacggg | 4350 |
| aagcatatgc tatcgaatta gggttagtaa aagggtccta aggaacagcg | 4400 |
| atatctccca ccccatgagc tgtcacggtt ttatttacat ggggtcagga | 4450 |
| ttccacgagg gtagtgaacc attttagtca caagggcagt ggctgaagat | 4500 |
| caaggagcgg gcagtgaact ctcctgaatc ttcgcctgct tcttcattct | 4550 |
| ccttcgttta gctaatagaa taactgctga gttgtgaaca gtaaggtgta | 4600 |
| tgtgaggtgc tcgaaaacaa ggtttcaggt gacgccccca gaataaaatt | 4650 |
| tggacggggg gttcagtggt ggcattgtgc tatgacacca atataaccct | 4700 |
| cacaaacccc ttgggcaata aatactagtg taggaatgaa acattctgaa | 4750 |
| tatcttttaac aatagaaatc catggggtgg ggacaagccg taaagactgg | 4800 |
| atgtccatct cacacgaatt tatggctatg ggcaacacat aatcctagtg | 4850 |

```
caatatgata ctggggttat aagatgtgt cccaggcagg gaccaagaca       4900
ggtgaaccat gttgttacac tctatttgta acaaggggaa agagagtgga     4950
cgccgacagc agcggactcc actggttgtc tctaacaccc ccgaaaatta     5000
aacgggctc cacgccaatg gggcccataa acaaagacaa gtggccactc      5050
ttttttttga aattgtggag tggggcacg cgtcagcccc cacacgccgc       5100
cctgcggttt tggactgtaa aataaggtg taataacttg gctgattgta      5150
accccgctaa ccactgcggt caaaccactt gcccacaaaa ccactaatgg      5200
cacccgggg aatacctgca taagtaggtg ggcgggccaa gatagggggcg      5250
cgattgctgc gatctggagg acaaattaca cacacttgcg cctgagcgcc      5300
aagcacaggg ttgttggtcc tcatattcac gaggtcgctg agagcacggt      5350
gggctaatgt tgccatgggt agcatatact acccaaatat ctggatagca      5400
tatgctatcc taatctatat ctgggtagca taggctatcc taatctatat      5450
ctgggtagca tatgctatcc taatctatat ctgggtagta tatgctatcc      5500
taatttatat ctgggtagca taggctatcc taatctatat ctgggtagca      5550
tatgctatcc taatctatat ctgggtagta tatgctatcc taatctgtat      5600
ccgggtagca tatgctatcc taatagagat tagggtagta tatgctatcc      5650
taatttatat ctgggtagca tatactaccc aaatatctgg atagcatatg      5700
ctatcctaat ctatatctgg gtagcatatg ctatcctaat ctatatctgg      5750
gtagcatagg ctatcctaat ctatatctgg gtagcatatg ctatcctaat      5800
ctatatctgg gtagtatatg ctatcctaat ttatatctgg gtagcatagg      5850
ctatcctaat ctatatctgg gtagcatatg ctatcctaat ctatatctgg      5900
gtagtatatg ctatcctaat ctgtatccgg gtagcatatg ctatcctcat      5950
gcatatacag tcagcatatg atacccagta gtagagtggg agtgctatcc      6000
tttgcatatg ccgccacctc ccaagggggc gtgaattttc gctgcttgtc      6050
cttttcctgc tggttgctcc cattcttagg tgaatttaag gaggccaggc      6100
taaagccgtc gcatgtctga ttgctcacca ggtaaatgtc gctaatgttt      6150
tccaacgcga aaggtgttg agcgcggagc tgagtgacgt gacaacatgg       6200
gtatgcccaa ttgccccatg ttgggaggac gaaaatggtg acaagacaga     6250
tggccagaaa tacaccaaca gcacgcatga tgtctactgg ggatttattc      6300
tttagtgcgg gggaatacac ggcttttaat acgattgagg gcgtctccta     6350
acaagttaca tcactcctgc ccttcctcac cctcatctcc atcacctcct      6400
tcatctccgt catctccgtc atcacccctcc gcggcagccc cttccaccat     6450
aggtggaaac cagggaggca aatctactcc atcgtcaaag ctgcacacag      6500
tcaccctgat attgcaggta ggagcgggct ttgtcataac aaggtcctta     6550
atcgcatcct tcaaaacctc agcaaatata tgagtttgta aaagaccat      6600
gaaataacag acaatggact cccttagcgg gccaggttgt gggccgggtc     6650
caggggccat tccaaagggg agacgactca atggtgtaag acgacattgt      6700
ggaatagcaa gggcagttcc tcgccttagg ttgtaaaggg aggtcttact      6750
acctccatat acgaacacac cggcgaccca agttccttcg tcggtagtcc      6800
```

| | |
|---|---|
| tttctacgtg actcctagcc aggagggccc ttaaaccttc tgcaatgttc | 6850 |
| tcaaatttcg ggttggaacc tccttgacca cgatgctttc caaaccaccc | 6900 |
| tccttttttg cgcctgcctc catcaccctg accccggggt ccagtgcttg | 6950 |
| ggccttctcc tgggtcatct gcggggccct gctctatcgc tcccggggggc | 7000 |
| acgtcaggct caccatctgg gccaccttct tggtggtatt caaaataatc | 7050 |
| ggcttcccct acagggtgga aaaatggcct tctacctgga gggggcctgc | 7100 |
| gcggtggaga cccggatgat gatgactgac tactgggact cctgggcctc | 7150 |
| ttttctccac gtccacgacc tctccccctg gctctttcac gacttccccc | 7200 |
| cctggctctt tcacgtcctc taccccggcg gcctccacta cctcctcgac | 7250 |
| cccggcctcc actacctcct cgaccccggc ctccactgcc tcctcgaccc | 7300 |
| cggcctccac ctcctgctcc tgcccctcct gtcctgcccc ctcctcctgc | 7350 |
| tcctgcccct cctgcccctc ctgctcctgc ccctcctgcc cctcctgctc | 7400 |
| ctgcccctcc tgcccctcct gctcctgccc tcctgcccc tcctcctgct | 7450 |
| cctgcccctc ctgcccctcc tcctgctcct gcccctcctg ccctcctgc | 7500 |
| tcctgcccct cctgcccctc ctgctcctgc cctcctgcc cctcctgctc | 7550 |
| ctgcccctcc tgctcctgcc cctcctgctc ctgcccctc tgctcctgcc | 7600 |
| cctcctgccc ctcctgcccc tcctcctgct cctgcccctc ctgctcctgc | 7650 |
| ccctcctgcc cctcctgccc ctcctgctcc tgcccctcct cctgctcctg | 7700 |
| ccctcctgc cctcctgcc cctcctgctc ctgcccctc ctgcccct | 7750 |
| cctcctgctc ctgcccctcc tcctgctcct gcccctcctg ccctcctgc | 7800 |
| ccctcctcct gctcctgccc ctcctgcccc tcctcctgct cctgcccctc | 7850 |
| ctcctgctc tgcccctcct gcccctcctg ccctcctcc tgctcctgcc | 7900 |
| cctcctcctg ctcctgcccc tcctgcccct cctgccctc ctgcccctcc | 7950 |
| tcctgctcct gcccctcctc ctgctcctgc cctcctgct cctgcccctc | 8000 |
| ccgctcctgc tcctgctcct gttccaccgt gggtcccttt gcagccaatg | 8050 |
| caacttggac gttttgggg tctccggaca ccatctctat gtcttggccc | 8100 |
| tgatcctgag ccgcccgggg ctcctggtct tccgcctcct cgtcctcgtc | 8150 |
| ctcttccccg tcctcgtcca tggttatcac cccctcttct ttgaggtcca | 8200 |
| ctgccgccgg agccttctgg tccagatgtg tctcccttct ctcctaggcc | 8250 |
| atttccaggt cctgtacctg gccctcgtc agacatgatt cacactaaaa | 8300 |
| gagatcaata gacatctta ttagacgacg ctcagtgaat acagggagtg | 8350 |
| cagactcctg ccccctccaa cagcccccc accctcatcc ccttcatggt | 8400 |
| cgctgtcaga cagatccagg tctgaaaatt ccccatcctc cgaaccatcc | 8450 |
| tcgtcctcat caccaattac tcgcagcccg gaaaactccc gctgaacatc | 8500 |
| ctcaagattt gcgtcctgag cctcaagcca ggcctcaaat tcctcgtccc | 8550 |
| cctttttgct ggacggtagg gatgggatt ctcgggaccc ctcctcttcc | 8600 |
| tcttcaaggt caccagacag agatgctact ggggcaacgg aagaaaagct | 8650 |
| gggtgcggcc tgtgaggatc agcttatcga tgataagctg tcaaacatga | 8700 |
| gaatt | 8705 |

-continued

```
<210> SEQ ID NO 15
<211> LENGTH: 29
<212> TYPE: DNA
<213> ORGANISM: Artificial Sequence
<220> FEATURE:
<223> OTHER INFORMATION: CatCass1

<400> SEQUENCE: 15
ctgatgaggt cgcgactagt gttgacaat                                        29

<210> SEQ ID NO 16
<211> LENGTH: 27
<212> TYPE: DNA
<213> ORGANISM: Artificial Sequence
<220> FEATURE:
<223> OTHER INFORMATION: CatCass2

<400> SEQUENCE: 16
ttcggtctcg cgagcaggtt agtgaca                                          27

<210> SEQ ID NO 17
<211> LENGTH: 5658
<212> TYPE: DNA
<213> ORGANISM: Artificial Sequence
<220> FEATURE:
<223> OTHER INFORMATION: pBK

<400> SEQUENCE: 17
ctagttctgg cgcagaacca tggcctttgt ccagtttaac tggggacaag                  50
gccaagattc ctaggctcgc aaaacatgtc tgtcatgcac tttccttcct                 100
gaggtcatgg tttggctgca ttccatgggt aagcagctcc tccctgtgag                 150
tcatgcactt tccttcctga ggtcatggtt tggctgcatt cccctgtgag                 200
tcatgcactt tccttcctga ggtcatggtt tggctgcatt ccatgggtaa                 250
gcagctcctc cctgtggcct tttttttat aatatataag aggccgaggc                  300
cgcctctgcc tccacccttt ctctcaagta gtaagggtgt ggaggctttt                 350
tctgaggcct agcaaaacta tttggggaaa tccctattct tttgcaattt                 400
ttgcaaaaat ggataaagtt cttaacaggg aagaatccat ggagctcatg                 450
gaccttttag gccttgaaag agctgcctgg ggaaatcttc ccttaatgag                 500
aaaagcttat ttaaggaagt gtaaggaatt tcatcctgac aaagggggcg                 550
acgaggataa aatgaagaga atgaatactt tgtataaaaa aatggagcag                 600
gatgtaaagg tagctcatca gcctgatttt ggaacttgga gtagctcaga                 650 ggttttgtgct gattttcctc tttgcccaga tacctgtac tgcaaggaat                  700 ggcctatttg ttccaaaaag ccttctgtgc actgcccttg catgctatgt                 750
cagcttagat taaggcattt aaatagaaaa ttttaagaa aagagccctt                   800 ggtttggata gattgctact gcattgactg cttcacacag tggtttggct                 850
tagacctaac tgaagaaact ctgcaatggt gggtccaaat aattggagaa                 900
actcccttca gagatctaaa gctttaaggt aactaactta tatttagata                 950
aataataaaa tattaaaagg ccctaagtaa ttatttttt tataggtgcc                  1000 aacctatgga acagaagagt gggagtcctg gtggagttcc tttaatgaaa                1050
aatgggatga agatttattt tgccatgaag atatgtttgc cagtgatgaa                1100
gaagcaacag cagattctca acactcaaca ccacccaaaa aaaaagaaa                 1150
```

-continued

| | |
|---|---|
| ggtagaagac cctaaagact ttccctctga tctacaccag tttcttagtc | 1200 |
| aagctgtatt tagtaataga acccttgcct gctttgctgt gtatactact | 1250 |
| aaagaaaaag ctcaaattct gtataaaaaa cttatggaaa atattctgt | 1300 |
| aactttatt agtagacaca tgtgtgctgg gcataatatt atattctttt | 1350 |
| taactccaca tagacataga gtttctgcaa ttaataattc ctgtcaaaag | 1400 |
| ctgtgtacct ttagttttt aatttgtaag ggtgttaata aggaatactt | 1450 |
| actatatagt gccttaacta gagatccata ccatactata gaagaaagca | 1500 |
| ttcaagggg cttaaaggag catgatttta gcccagaaga gcctgaagaa | 1550 |
| acaaagcagg tgtcttggaa attaattact gagtatgcag tagagacaaa | 1600 |
| gtgtgaggat gtgttttat tattaggtat gtatttagaa tttcaataca | 1650 |
| atgtagagga gtgtaaaaag tgtcagaaaa aagaccagcc ttatcacttt | 1700 |
| aagtatcatg aaaagcactt tgcaaatgct attattttg cagaaagtaa | 1750 |
| aaatcaaaaa agtatttgtc agcaagcagt agatacagtt ttagctaaaa | 1800 |
| aaagagtaga taccttcat atgaccaggg aagaaatgct aacagaaaga | 1850 |
| ttcaatcata tattagataa aatggattta atatttggag ctcatggaaa | 1900 |
| tgctgtacta gaacaatata tggcaggtgt tgcttggctg cactgtttgc | 1950 |
| tacctaaaat ggattctgta atatttgatt ttttgcactg tattgttttc | 2000 |
| aatgtaccta aaagaagata ctggttattt aaaggtccca ttgatagtgg | 2050 |
| aaaaacaaca ctagctgccg ggttattaga tttgtgtggt ggtaaagcct | 2100 |
| taaatgtaaa cctacccatg gaaaggctaa cctttgagct aggtgtagct | 2150 |
| atagatcagt acatggttgt ttttgaagat gtaaagggga caggagctga | 2200 |
| atcaaaggat ttgccttcag gacatggaat aaacaattta gacagtttga | 2250 |
| gagattattt agatggaagt gttaaggtaa atttagaaaa gaaacattta | 2300 |
| aacaaaagaa cccaaatatt tccaccaggc ttggttacaa tgaatgagta | 2350 |
| tcctgtccct aaaaccctgc aagctagatt tgtaagacaa atagatttta | 2400 |
| ggcccaaaat atatttaaga aaatccttac aaaactcaga gttcttactt | 2450 |
| gaaaaaagaa ttttacaaag tggaatgacc ttgttgctac tgctaatttg | 2500 |
| gtttaggcct gtagctgatt ttgcaactga tatacaatct agaattgttg | 2550 |
| aatggaagga aaggctggat tctgagataa gtatgtatac tttttcaagg | 2600 |
| atgaaatata atatatgctt ggggaaatgt attcttgata ttacaagaga | 2650 |
| agaggattca gaaactgaag actctggaca tggatcaagc actgaatccc | 2700 |
| aatcacaatg ctcttcccaa gtctcagata cttcagcccc tgctgaagat | 2750 |
| tcccaaaggt cagaccccca tagtcaagag ttgcatttgt gtaaaggctt | 2800 |
| tcagtgtttt aaaaggccta aaacaccacc cccaaaataa cacaagctta | 2850 |
| aaagtggctt atacaaaagc agcatttatt aaatgtatat gtacaataaa | 2900 |
| agcacctgtt taaagcattt tggtttgcaa ttgtccctgt ttgtcaatat | 2950 |
| atcttatcat atctgggtcc cctggaagta actagatgat ccgctgtgga | 3000 |
| atgtgtgtca gttagggtgt ggaaagtccc caggctcccc agcaggcaga | 3050 |
| agtatgcaaa gcatctcaat tagtcagcaa ccaggtgtgg aaagtcccca | 3100 |
| ggctccccag caggcagaag tatgcaaagt aatagtaatc aattacgggg | 3150 |

-continued

```
tcattagttc atagcccata tatggagttc cgcgttacat aacttacggt           3200
aaatggcccg cctggctgac cgcccaacga ccccccgccca ttgacgtcaa          3250 taatgacgta tgttcccata gtaacgccaa tagggacttt ccattgacgt          3300
caatgggtgg agtatttacg gtaaactgcc cacttggcag tacatcaagt          3350
gtatcatatg ccaagtacgc ccctattga cgtcaatgac ggtaaatggc           3400
ccgcctggca ttatgcccag tacatgacct tatgggactt tcctacttgg          3450
cagtacatct acgtattagt catcgctatt accatggcga tgcggttttg          3500
gcagtacatc aatgggcgtg gatagcggtt tgactcacgg ggatttccaa          3550
gtctccaccc cattgacgtc aatgggagtt tgttttggca ccaaaatcaa          3600
cgggactttc caaaatgtcg taacaactcc gccccattga cgcaaatggg          3650
cggtaggcgt gtacggtggg aggtctatat aagcagagct ggtttagtga          3700
accgtcagat ccgctagcgc taccggactc agatctcgag ctcaagctaa          3750
tcatcggcat agtatatcgg catagtataa tacgactcac tataggaggg          3800
ccaccatggc caagttgacc agtgccgttc cggtgcttac cgcgcgcgac          3850
gtcgccggag cggtcgagtt ctggaccgac cggctcgggt tctcccggga          3900
cttcgtggag gacgacttcg ccggtgtggt ccgggacgac gtgaccctgt          3950
tcatcagcgc ggtccaggac caggtggtgc cggacaacac cctggcctgg          4000
gtgtgggtgc gcggcctgga cgagctgtac gccgagtggt cggaggtcgt          4050
gtccacgaac ttccgggacg cctccgggcc ggccatgacc gagatcggcg          4100
agcagccgtg ggggcgggag ttcgccctgc gcgacccggc cggcaactgc          4150
gtgcacttcg tggccgagga gcaggactga ccgacgccga ccaacaccgc          4200
cggggggagg ctaactgaaa cacggaagga gacaataccg gaaggaaccc          4250
gcgctatgac ggcaataaaa agacagaata aaacgcacgg tgttgggtcg          4300
tttgttcata aacgcggggt tcggtcccag ggctggcact ctgtcgatac          4350
cccaccgacg gcggcccacg ggtcgaattg cgcttccctg atgagaccga          4400
aaggtcgaaa gtcgaaagac tcggaagcga aagcttggtg atgcattcga          4450
tatcgtttaa acgcccgggc gcggccgcgg cgcctccagt cgacgaaagt          4500
cggtctgccg aaaggcactg atgagtccga aaggacgaaa ccgacttgct          4550
agataactga tcataatcag ccataccaca tttgtagagg ttttacttgc          4600
tttaaaaaac ctcccacacc tccccctgaa cctgaaacat aaaatgaatg          4650
caattgttgt tgttaacttg tttattgcag cttataatgg ttacaaataa          4700
agcaatagca tcacaaattt cacaaataaa gcatttttt cactgcattc           4750 tagttgtggt ttgtccaaac tcatcaatgt atcttaacgc gtaaattgta          4800
agcgttaatc atgcggccca tgaccaaaat cccttaacgt gagttttcgt          4850
tccactgagc gtcagacccc gtagaaaaga tcaaaggatc ttcttgagat          4900 ccttttttc tgcgcgtaat ctgctgcttg caaacaaaaa aaccaccgct           4950
accagcggtg gtttgtttgc cggatcaaga gctaccaact ctttttccga          5000
aggtaactgg cttcagcaga gcgcagatac caaatactgt ccttctagtg          5050
tagccgtagt taggccacca cttcaagaac tctgtagcac cgcctacata          5100
```

```
cctcgctctg ctaatcctgt taccagtggc tgctgccagt ggcgataagt           5150
cgtgtcttac cgggttggac tcaagacgat agttaccgga taaggcgcag           5200
cggtcgggct gaacgggggg ttcgtgcaca cagcccagct tggagcgaac           5250
gacctacacc gaactgagat acctacagcg tgagcattga gaaagcgcca           5300
cgcttcccga agggagaaag gcggacaggt atccggtaag cggcagggtc           5350
ggaacaggag agcgcacgag ggagcttcca gggggaaacg cctggtatct           5400
ttatagtcct gtcgggtttc gccacctctg acttgagcgt cgatttttgt           5450
gatgctcgtc agggggggcgg agcctatgga aaaacgccag caacgcggcc          5500
tttttacggt tcctggcctt tgctggcct tttgctcaca tgttctttcc            5550
tgcgttatcc cctgattctg tggataaccg tattaccgcc tttgagtgag           5600
ctgataccgc tcgccgcagc cgaacgaccg agcgcagcga gtcagtgagc           5650
gaggaagc                                                         5658

<210> SEQ ID NO 18
<211> LENGTH: 178
<212> TYPE: DNA
<213> ORGANISM: Artificial Sequence
<220> FEATURE:
<223> OTHER INFORMATION: Multi-cloning sequence flanked by two
      cis-acting ribozymes (CAR'a).

<400> SEQUENCE: 18
gagctcgctt ccctgatgag tccgaaagga cgaaagtcga aagactcgga             50
agcgaaagct tggtgatgca ttcgatatcg tttaaacgcc cggcgcggc            100 cgcggcgcct ccagtcgacg aaagtcggtc tgccgaaagg cactgatgag           150
tccgaaagga cgaaaccgac ttggtacc                                   178

<210> SEQ ID NO 19
<211> LENGTH: 14
<212> TYPE: DNA
<213> ORGANISM: herpes simplex virus

<400> SEQUENCE: 19
cgacgccgcc cgcc                                                   14

<210> SEQ ID NO 20
<211> LENGTH: 13
<212> TYPE: DNA
<213> ORGANISM: herpes simplex virus

<400> SEQUENCE: 20
cugcgcgcgu ggc                                                    13

<210> SEQ ID NO 21
<211> LENGTH: 14
<212> TYPE: DNA
<213> ORGANISM: herpes simplex virus

<400> SEQUENCE: 21
gcgccugcgc gggg                                                   14

<210> SEQ ID NO 22
<211> LENGTH: 14
<212> TYPE: DNA
<213> ORGANISM: herpes simplex virus
```

-continued

<400> SEQUENCE: 22
cgccgccgac gcgc                                          14

<210> SEQ ID NO 23
<211> LENGTH: 13
<212> TYPE: DNA
<213> ORGANISM: herpes simplex virus

<400> SEQUENCE: 23
cccccucccc gcg                                           13

<210> SEQ ID NO 24
<211> LENGTH: 14
<212> TYPE: DNA
<213> ORGANISM: herpes simplex virus

<400> SEQUENCE: 24
guggccgugu cgcg                                          14

<210> SEQ ID NO 25
<211> LENGTH: 14
<212> TYPE: DNA
<213> ORGANISM: herpes simplex virus

<400> SEQUENCE: 25
gccacacggc ggcg                                          14

<210> SEQ ID NO 26
<211> LENGTH: 14
<212> TYPE: DNA
<213> ORGANISM: herpes simplex virus

<400> SEQUENCE: 26
cgccgcgcgg ugcg                                          14

<210> SEQ ID NO 27
<211> LENGTH: 14
<212> TYPE: DNA
<213> ORGANISM: herpes simplex virus

<400> SEQUENCE: 27
cgccgcgcgg ugcg                                          14

<210> SEQ ID NO 28
<211> LENGTH: 15
<212> TYPE: DNA
<213> ORGANISM: herpes simplex virus

<400> SEQUENCE: 28
cccccugcgc gccuc                                         15

<210> SEQ ID NO 29
<211> LENGTH: 15
<212> TYPE: DNA
<213> ORGANISM: herpes simplex virus

<400> SEQUENCE: 29
gguggugcug uacuc                                         15

<210> SEQ ID NO 30
<211> LENGTH: 14
<212> TYPE: DNA
<213> ORGANISM: herpes simplex virus

```
<400> SEQUENCE: 30
gggcccgcgg uguc                                                14

<210> SEQ ID NO 31
<211> LENGTH: 14
<212> TYPE: DNA
<213> ORGANISM: herpes simplex virus

<400> SEQUENCE: 31
ccuggcgugc gagc                                                14

<210> SEQ ID NO 32
<211> LENGTH: 21
<212> TYPE: DNA
<213> ORGANISM: herpes simplex virus

<400> SEQUENCE: 32
ggggaccacc gacgccaugg c                                        21

<210> SEQ ID NO 33
<211> LENGTH: 14
<212> TYPE: DNA
<213> ORGANISM: herpes simplex virus

<400> SEQUENCE: 33
cguggcgcug gggc                                                14

<210> SEQ ID NO 34
<211> LENGTH: 14
<212> TYPE: DNA
<213> ORGANISM: herpes simplex virus

<400> SEQUENCE: 34
cgggauucgc uggg                                                14

<210> SEQ ID NO 35
<211> LENGTH: 15
<212> TYPE: DNA
<213> ORGANISM: Artificial Sequence
<220> FEATURE:
<223> OTHER INFORMATION: Portion of a multiple cloning site for use in
      making deletion libraries.

<400> SEQUENCE: 35
ggtgatgcat tcgat                                               15

<210> SEQ ID NO 36
<211> LENGTH: 38
<212> TYPE: DNA
<213> ORGANISM: Artificial Sequence
<220> FEATURE:
<223> OTHER INFORMATION: Portion of a multiple cloning site for use in
      making deletion libraries.

<400> SEQUENCE: 36
atcgtttaaa cgcccgggcg cggccgcggc gcctccag                      38

<210> SEQ ID NO 37
<211> LENGTH: 10
<212> TYPE: DNA
<213> ORGANISM: Artificial Sequence
<220> FEATURE:
<223> OTHER INFORMATION: Portion of a multiple cloning site for use in
      making deletion libraries.
```

```
<400> SEQUENCE: 37
ctggaggcgc                                                              10

<210> SEQ ID NO 38
<211> LENGTH: 22
<212> TYPE: DNA
<213> ORGANISM: Artificial Sequence
<220> FEATURE:
<221> NAME/KEY: misc_feature
<222> LOCATION: 1..16
<223> OTHER INFORMATION: Portion of an intermediate in the making of a
      deletion library, including a portion of a multiple cloning site.

<400> SEQUENCE: 38
nnnnnnnnnn nnnnnnctcc ag                                                22

<210> SEQ ID NO 39
<211> LENGTH: 25
<212> TYPE: DNA
<213> ORGANISM: Artificial Sequence
<220> FEATURE:
<221> NAME/KEY: misc_feature
<222> LOCATION: 6..19
<223> OTHER INFORMATION: 14 bp variable sequence fragment of a deletion
      library including flanking portions of multiple cloning site.

<400> SEQUENCE: 39
ggtgannnnn nnnnnnnnnc tccag                                             25

<210> SEQ ID NO 40
<211> LENGTH: 35
<212> TYPE: RNA
<213> ORGANISM: Artificial Sequence
<220> FEATURE:
<221> NAME/KEY: misc_feature
<222> LOCATION: 1..7 and 31..35
<223> OTHER INFORMATION: A hammerhead ribozyme comprising a catalytic
      core flanked by variable recognition domains.

<400> SEQUENCE: 40
nnnnnnncug augaggucgc gagaccgaaa nnnnn                                  35

<210> SEQ ID NO 41
<211> LENGTH: 14
<212> TYPE: RNA
<213> ORGANISM: Artificial Sequence
<220> FEATURE:
<221> NAME/KEY: misc_feature
<222> LOCATION: 1..5 and 8..14
<223> OTHER INFORMATION: A target substrate comprising variable
      sequence regions flanking a cleavage site.

<400> SEQUENCE: 41
nnnnnuhnnn nnnn                                                         14

<210> SEQ ID NO 42
<211> LENGTH: 12
<212> TYPE: DNA
<213> ORGANISM: Artificial Sequence
<220> FEATURE:
<221> NAME/KEY: misc_feature
<222> LOCATION: 6..12
<223> OTHER INFORMATION: A portion of an antisense library including an
      HphI site.

<400> SEQUENCE: 42
ggtgannnnn nn                                                           12
```

<210> SEQ ID NO 43
<211> LENGTH: 12
<212> TYPE: DNA
<213> ORGANISM: Artificial Sequence
<220> FEATURE:
<221> NAME/KEY: misc_feature
<222> LOCATION: 1..6
<223> OTHER INFORMATION: A portion of an antisense library including a
      BpmI site.

<400> SEQUENCE: 43
nnnnnnctcc ag                                                         12

<210> SEQ ID NO 44
<211> LENGTH: 15
<212> TYPE: DNA
<213> ORGANISM: Artificial Sequence
<220> FEATURE:
<223> OTHER INFORMATION: A sequence flanking a chloramphenicol (CAT)
      gene and containing an NruI site.

<400> SEQUENCE: 44
ctgatgaggt cgcga                                                      15

<210> SEQ ID NO 45
<211> LENGTH: 14
<212> TYPE: DNA
<213> ORGANISM: Artificial Sequence
<220> FEATURE:
<223> OTHER INFORMATION: A sequence flanking a chloramphenicol (CAT)
      gene and containing an NruI site.

<400> SEQUENCE: 45
tcgcgagagc cgaa                                                       14

<210> SEQ ID NO 46
<211> LENGTH: 27
<212> TYPE: DNA
<213> ORGANISM: Artificial Sequence
<220> FEATURE:
<221> NAME/KEY: misc_feature
<222> LOCATION: 6..12
<223> OTHER INFORMATION: Sequence flanking a chloramphenicol (CAT) gene
      after insertion into the antisense library.

<400> SEQUENCE: 46
ggtgannnnn nnctgatgag gtcgcga                                         27

<210> SEQ ID NO 47
<211> LENGTH: 25
<212> TYPE: DNA
<213> ORGANISM: Artificial Sequence
<220> FEATURE:
<221> NAME/KEY: misc_feature
<222> LOCATION: 14..19
<223> OTHER INFORMATION: Sequence flanking the chloramphenicol (CAT)
      gene after insertion into the antisense library.

<400> SEQUENCE: 47
tcgcgagacc gaannnnnnc tccag                                           25

<210> SEQ ID NO 48
<211> LENGTH: 46
<212> TYPE: DNA
<213> ORGANISM: Artificial Sequence
<220> FEATURE:
<221> NAME/KEY: misc_feature -continued

```
<222> LOCATION: 6..12 and 35..40
<223> OTHER INFORMATION: Hammerhead ribozyme library with flanking
      sequences.

<400> SEQUENCE: 48
ggtgannnnn nnctgatgag gtcgcgagac cgaannnnnn ctccag                        46

<210> SEQ ID NO 49
<211> LENGTH: 20
<212> TYPE: DNA
<213> ORGANISM: Artificial Sequence
<220> FEATURE:
<221> NAME/KEY: misc_feature
<222> LOCATION: 1..14
<223> OTHER INFORMATION: Deletion fragment in a deletion fragment
      library, including a portion of a multiple cloning site.

<400> SEQUENCE: 49
nnnnnnnnnn nnnnctccag                                                    20

<210> SEQ ID NO 50
<211> LENGTH: 53
<212> TYPE: DNA
<213> ORGANISM: Artificial Sequence
<220> FEATURE:
<223> OTHER INFORMATION: Multiple cloning site for use in making
      deletion libraries.

<400> SEQUENCE: 50
tgcattcgat atcgtttaaa cgcccgggcg cggccgcggc                              40
gcctccagtc gac                                                           53
```